United States Patent
Yoshikawa et al.

(10) Patent No.: US 9,962,131 B2
(45) Date of Patent: May 8, 2018

(54) X-RAY PHOTOGRAPHY APPARATUS, IMAGE PROCESSING DEVICE, AND X-RAY PHOTOGRAPHY METHOD

(71) Applicant: J. Morita Manufacturing Corporation, Kyoto-shi, Kyoto (JP)

(72) Inventors: Hideki Yoshikawa, Kyoto (JP); Tomoyuki Sadakane, Kyoto (JP); Yoshito Sugihara, Kyoto (JP)

(73) Assignee: J. Morita Manufacturing Corporation (JP)

( * ) Notice: Subject to any disclaimer, the term of this patent is extended or adjusted under 35 U.S.C. 154(b) by 138 days.

(21) Appl. No.: 14/952,563

(22) Filed: Nov. 25, 2015

(65) Prior Publication Data

US 2016/0151027 A1 Jun. 2, 2016

(30) Foreign Application Priority Data

Nov. 28, 2014 (JP) .................................. 2014-242137
Nov. 25, 2015 (JP) .................................. 2015-229857

(51) Int. Cl.

| A61B 6/00 | (2006.01) |
|---|---|
| A61B 6/02 | (2006.01) |
| A61B 6/03 | (2006.01) |
| A61B 6/04 | (2006.01) |
| A61B 6/14 | (2006.01) |

(52) U.S. Cl.
CPC ............ *A61B 6/4035* (2013.01); *A61B 6/027* (2013.01); *A61B 6/032* (2013.01); *A61B 6/04* (2013.01);
(Continued)

(58) Field of Classification Search
CPC ......... A61B 6/14; A61B 6/4441; A61B 6/032; A61B 6/145; A61B 6/4233; A61B 6/588;
(Continued)

(56) References Cited

U.S. PATENT DOCUMENTS

| 2013/0307923 A1 | 11/2013 | Inglese et al. |
| 2015/0078516 A1* | 3/2015 | Ohashi ................. A61B 6/06 378/42 |

FOREIGN PATENT DOCUMENTS

| EP | 0211956 A1 | 10/1985 |
| EP | 0211956 A1 | 3/1987 |

(Continued)

OTHER PUBLICATIONS

English translation of Japanese Office Action dated Nov. 22, 2016 issued in counterpart Japanese Patent Application No. 2015-229857.

(Continued)

*Primary Examiner* — Hoon Song
(74) *Attorney, Agent, or Firm* — DLA Piper LLP (US)

(57) ABSTRACT

An X-ray generator generating an X-ray cone beam and a two-dimensional X-ray detector detecting the X-ray cone beam are supported by a support arm while facing each other, and the X-ray generator and the two-dimensional X-ray detector are turned with an object interposed therebetween. A filter constitution body is disposed between the two-dimensional X-ray detector and the object. Filters having X-ray beam energy distribution conversion characteristics different from each other are arrayed in the filter constitution body. In X-ray photography, a filter constitution body moving mechanism is moved in a direction along a detection surface of the two-dimensional X-ray detector such that the filter constitution body traverses the X-ray cone beam in turning the support arm.

18 Claims, 21 Drawing Sheets

(52) U.S. Cl.
CPC .............. *A61B 6/14* (2013.01); *A61B 6/4085* (2013.01); *A61B 6/42* (2013.01); *A61B 6/4429* (2013.01); *A61B 6/482* (2013.01); *A61B 6/501* (2013.01); *A61B 6/5205* (2013.01); *A61B 6/54* (2013.01)

(58) Field of Classification Search
CPC ........... A61B 6/06; A61B 6/469; A61B 6/587; A61B 6/542; A61B 6/4035
See application file for complete search history.

(56) References Cited

FOREIGN PATENT DOCUMENTS

| | | |
|---|---|---|
| JP | 60220049 A | 11/1985 |
| JP | 63046136 A | 2/1988 |
| JP | 63082628 A | 4/1988 |
| JP | 11267120 A | 10/1999 |
| JP | 11332861 A | 12/1999 |
| JP | 2003000587 A | 1/2003 |
| JP | 2006110324 A | 4/2006 |
| JP | 2014501142 A | 1/2014 |
| KR | 20140044175 A | 4/2014 |
| WO | 2012114250 A1 | 8/2012 |

OTHER PUBLICATIONS

Extended European Search Report dated Apr. 12, 2016 issued in counterpart European Patent Application No. 15196747.

* cited by examiner

F I G. 7
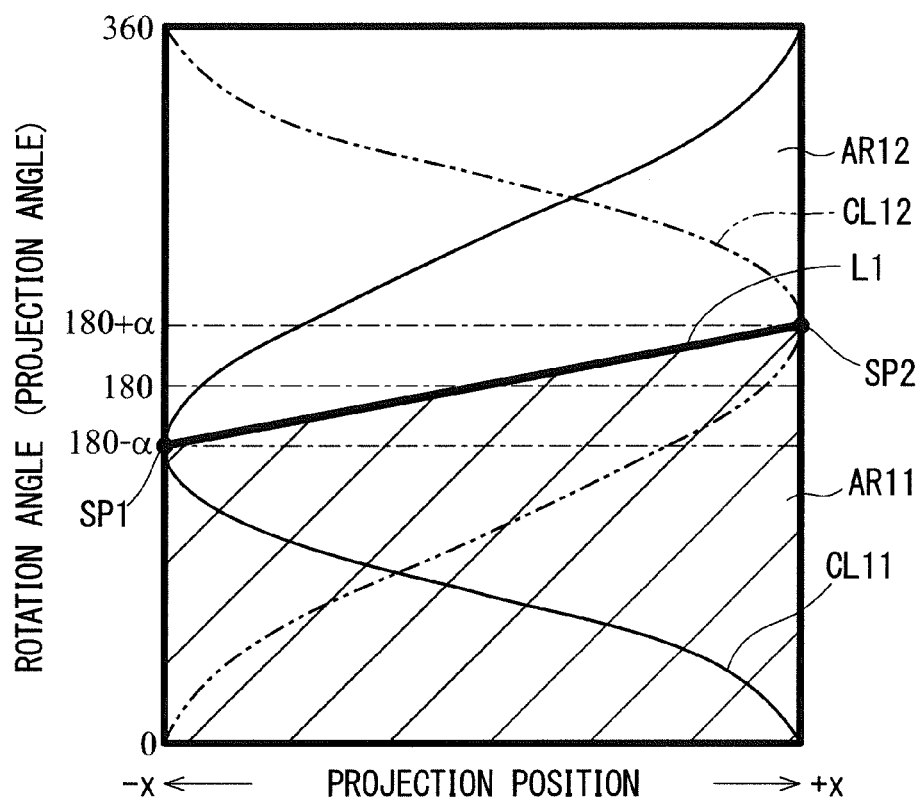

F I G. 1 0
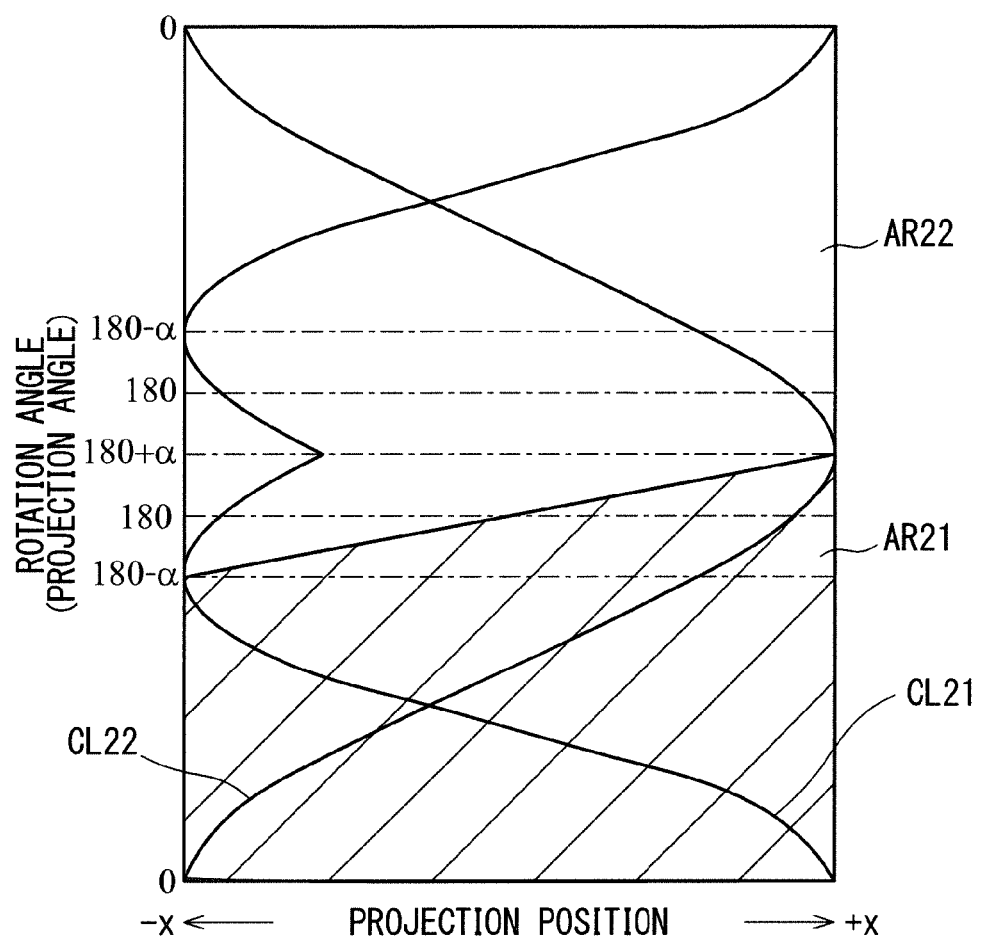

F I G. 1 8
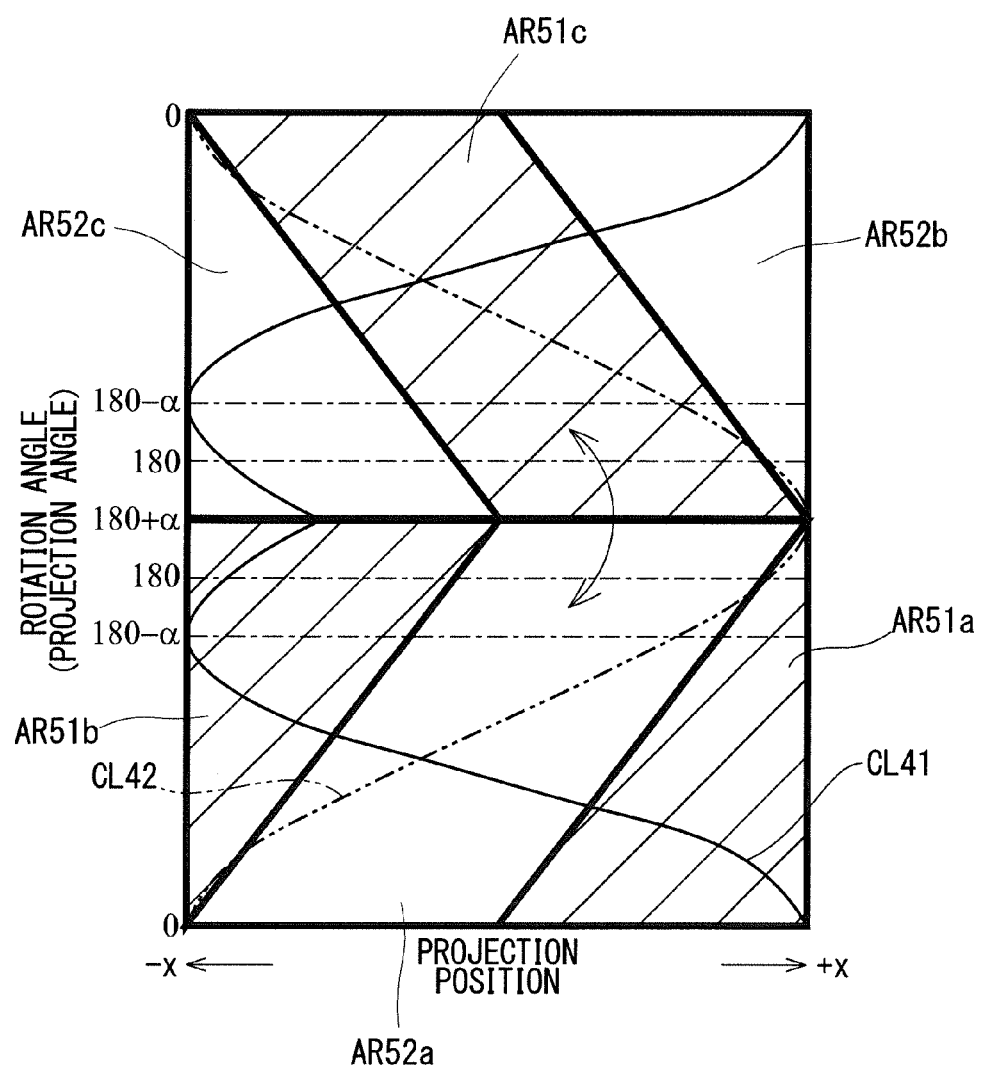

X-RAY PHOTOGRAPHY APPARATUS, IMAGE PROCESSING DEVICE, AND X-RAY PHOTOGRAPHY METHOD

BACKGROUND OF THE INVENTION

Field of the Invention

The present invention relates to a technology of an X-ray photography.

Description of the Background Art

Conventionally, CT scan (Computed Tomography) is performed using an X-ray photography apparatus for the purpose of a medical diagnosis or a non-destructive inspection. In the X-ray photography apparatus, multi energy scan that photographs an identical region of an object is performed with plural X-rays having different X-ray energy distributions (for example, see Japanese Patent Application Laid-Open No. 2008-54831).

In the multi energy scan, tomographic images corresponding to the X-rays having different energy distribution characteristics can be obtained with respect to an identical sectional surface in the identical region of the object. For example, an image of a specific region can be extracted by obtaining a difference between the tomographic images having the different energy distribution characteristics.

In an X-ray CT photography apparatus described in Japanese Patent Application Laid-Open No. 2008-54831, a subject is disposed between an X-ray tube of a radiation source and an X-ray detector of detection means for detecting a radiation. At this point, the X-ray tube and the X-ray detector are rotated by 360 degrees about a rotation axis set to a center of a CT scan area. Two kinds of filters are arrayed between the X-ray tube and the subject in order to vary the energy distribution of the transmitted X-ray each other. For this reason, the subject is simultaneously radiated from the right and left with the X-rays having the different energy distributions.

In a helical scan type X-ray CT apparatus, two detectors having different energy characteristics are continuously disposed in a slice direction to perform dual energy scan (for example, see Japanese Patent Application Laid-Open No. 6-296607 (1994)).

However, for the X-ray CT photography apparatus described in Japanese Patent Application Laid-Open No. 2008-54831, the X-ray is scattered in a boundary portion between the two kinds of filters. Because of a considerable distance from the two kinds of filters to the X-ray detector, the scattered X-ray is incident on a position distant from a position on which the X-ray should originally be incident. Therefore, there is a risk of blurring the obtained projection image.

In Japanese Patent Application Laid-Open No. 6-296607 (1994), the two detectors include two scintillators having different thicknesses or two filters in which at least X-ray absorptances, thicknesses, shapes, or materials differ from each other, thereby varying the energy characteristic. Therefore, the X-ray scattered in the boundary portion between the two filters or the two scintillators is intensively incident on a specific position of each detector. Therefore, there is a risk of hardly detecting the X-ray, which is transmitted through the photographing area where the X ray should originally be detected, at the scattered X-ray incident position of the detector.

SUMMARY OF THE INVENTION

The present invention is aimed at an X-ray photography apparatus.

According to a first aspect, an X-ray photography apparatus includes: an X-ray generator that generates and emits an X-ray beam to be transmitted through an object; a two-dimensional X-ray detector that receives and detects the X-ray beam; a support that supports the X-ray generator and the two-dimensional X-ray detector while the X-ray generator and the two-dimensional X-ray detector are arranged opposite each other; a moving mechanism that turns the support relative to the object while the object is interposed between the X-ray generator and the two-dimensional X-ray detector; a filter constitution body that is interposed between the object and the two-dimensional X-ray detector in a path of the X-ray beam, a first portion and a second portion being two-dimensionally arrayed in the filter constitution body, the first portion having a first energy distribution conversion characteristic of the X-ray beam, the second portion having a second energy distribution conversion characteristic of the X-ray beam; and a filter constitution body moving mechanism that moves the filter constitution body in a direction along a detection surface of the two-dimensional X-ray detector such that the filter constitution body traverses the X-ray beam during turning of the support during X-ray photography.

In the first aspect, the filter constitution body is moved during the X-ray photography so as to traverse the X-ray beam, which allows the movement of the boundary portion between the first portion and the second portion in the filter constitution body. Therefore, the intensive incidence of the X-ray, which is incident on and scattered by the boundary portion, on a specific position of the two-dimensional X-ray detector can be reduced. Accordingly, the influence of the scattered X-ray in the projection image data can be reduced.

For example, in a case to obtain two kinds of CT images (tomographic images) by reconstruction corresponding to the energy distribution characteristics of the X-rays passing through the first portion and the second portion, the two kinds of CT images can be cleared by reduction of influence of the scattered X-ray and the discretion of the energy of X-ray can be enhanced.

According to a second aspect, in the X-ray photography apparatus of the first aspect, the first portion includes a filter while the second portion does not include a filter.

In the second aspect, the X-rays each are incident on the first portion with the filter and the second portion without the filter. Therefore, the X-rays can be converted into the X-rays having the energy distribution characteristics different from each other.

According to a third aspect, in the X-ray photography apparatus of the first or second aspect, the first portion includes a first filter, the first filter having the first energy distribution conversion characteristic, and wherein the second portion includes a second filter, the second filter having the second energy distribution conversion characteristic.

In the third aspect, the X-rays each are incident on the first and second filters. Therefore, the X-rays can be converted into the X-rays having the energy distribution characteristics different from each other.

According to a fourth aspect, in the X-ray photography apparatus of any one of the first to third aspects, the filter constitution body moving mechanism includes a motor and a transmission unit.

In the fourth aspect, the filter constitution body can easily be moved by the motor and the transmission unit.

According to a fifth aspect, in the X-ray photography apparatus of any one of the first to fourth aspects, the filter constitution body moving mechanism moves the filter constitution body between the two-dimensional X-ray detector and the object and in a vertical direction along a rotational axis of the support or in a horizontal direction orthogonal to the rotational axis of the support.

In the fifth aspect, the filter constitution body is disposed relatively close to the two-dimensional X-ray detector, so that the boundary portion between the first portion and the second portion can be brought close to the two-dimensional X-ray detector. Therefore, the incidence of the X-ray, which is scattered by the boundary portion, on the position distant from the position on which the X-ray should be originally incident in the two-dimensional X-ray detector can be reduced.

According to a sixth aspect, in the X-ray photography apparatus of the fifth aspect, the X-ray photography is CT scan, and the first portion and the second portion are arrayed in a striped pattern.

According to a seventh aspect, in the X-ray photography apparatus of the fifth aspect, the X-ray photography is CT scan, and the first portion and the second portion are arrayed in a checkered pattern.

According to an eighth aspect, in the X-ray photography apparatus of the sixth or seventh aspect, the filter constitution body moving mechanism and the two-dimensional X-ray detector are disposed in a chassis.

According to a ninth aspect, in the X-ray photography apparatus of the eighth aspect, the filter constitution body moves in a direction intersecting a moving direction of the two-dimensional X-ray detector in the chassis.

According to a tenth aspect, in the X-ray photography apparatus of the eighth aspect, the filter constitution body moves in a direction along or facing a moving direction of the two-dimensional X-ray detector in the chassis.

According to an eleventh aspect, the X-ray photography apparatus of any one of the first to tenth aspects further includes an irradiation field controller that regulates the X-ray beam emitted from the X-ray generator. At this point, the irradiation field controller shapes the X-ray beam into an X-ray cone beam.

In the eleventh aspect, the cone beam can be formed by the irradiation field controller. Therefore, the CT scan can be performed using the cone beam.

According to a twelfth aspect, in the X-ray photography apparatus of the eleventh aspect, the X-ray photography performed by the X-ray photography apparatus is CT scan, and the filter constitution body moving mechanism withdraws the filter constitution body from a position on which the X-ray cone beam transmitted through a CT scan area is incident.

In the twelfth aspect, filter constitution body is withdrawn from the position on which the cone beam is incident, which allows the CT scan to be performed with no use of the filter.

According to a thirteenth aspect, in the X-ray photography apparatus of the eleventh or twelfth aspect, panorama X-ray photography or cephalometric photography is performed using an X-ray slit beam formed by the irradiation field controller.

In the thirteenth aspect, the X-ray slit beam can be formed by the irradiation field controller. Therefore, the panorama X-ray photography and the cephalometric photography can be performed using the X-ray slit beam.

According to a fourteenth aspect, in the X-ray photography apparatus of the ninth aspect, when the filter constitution body moving mechanism moves the filter constitution body during CT scan, at least one of the first portion and the second portion is displaced by a width in the intersecting direction while the support turns substantially 180 degrees plus a fan angle of the X-ray beam, while the support further turns substantially 180 degrees plus a fan angle of the X-ray beam, the one is further displaced by the width in the intersecting direction, and the other of the first portion and the second portion receives a remaining X-ray beam, the remaining X-ray beam not including an X-ray beam incident on the one displaced.

According to a fifteenth aspect, in the X-ray photography apparatus of the tenth aspect, when the filter constitution body moving mechanism moves the filter constitution body during the CT scan, during rotation of the support, the first portion is displaced by a width of the first portion in the moving direction of the two-dimensional X-ray detector, and the second portion is displaced by the same width in the displacement direction of the first portion at the same time as the first portion is displaced.

The present invention is aimed at an image processing device.

According to a sixteenth aspect, an image processing device that processes image data acquired by the X-ray photography apparatus of any one of the first to fifteenth aspects, the image processing device includes an image processor that performs image processing on pieces of image data to produce X-ray images corresponding to each of energy distribution characteristics, the pieces of image data being obtained by detecting the X-ray beams using the two-dimensional X-ray detector, the X-ray beams being transmitted or passing through the first portion and the second portion of the filter constitution body.

According to a seventeenth aspect, in the image processing device of the sixteenth aspect, the image processor acquires an image of difference of the image data corresponding to each of the energy distribution characteristics, the image of difference being produced by calculation.

The present invention is also aimed at an X-ray photography method.

According to an eighteenth aspect, an X-ray photography method includes; rotating, about an object, an X-ray generator and a two-dimensional X-ray detector facing each other, the X-ray generator generating an X-ray beam, the two-dimensional X-ray detector detecting the X-ray beam transmitted through the object; and moving, during the rotating, a filter constitution body in a direction along a detection surface of the two-dimensional X-ray detector such that the filter constitution body traverses the X-ray beam, the filter constitution body being interposed between the object and the two-dimensional X-ray detector in a path of the X-ray beam, a first portion and a second portion being two-dimensionally arrayed in the filter constitution body, the first portion having a first energy distribution conversion characteristic of the X-ray beam, the second portion having a second energy distribution conversion characteristic of the X-ray beam.

Therefore, an object of the present invention is to provide a technology of reducing the influence of the scattered X-ray in the projection image data acquired by the multi energy scan.

These and other objects, features, aspects and advantages of the present invention will become more apparent from the following detailed description of the present invention when taken in conjunction with the accompanying drawings.

BRIEF DESCRIPTION OF THE DRAWINGS

FIG. 7 is a view schematically illustrating a sinogram obtained in the first CT scan example of FIGS. 6A to 6E;

FIG. 10 is a view schematically illustrating a sinogram obtained in the second CT scan example of FIG. 10;

FIG. 18 is a view schematically illustrating a sinogram obtained in the fifth CT scan example of FIGS. 16 and 17;

DESCRIPTION OF THE PREFERRED EMBODIMENTS

Figure 1:
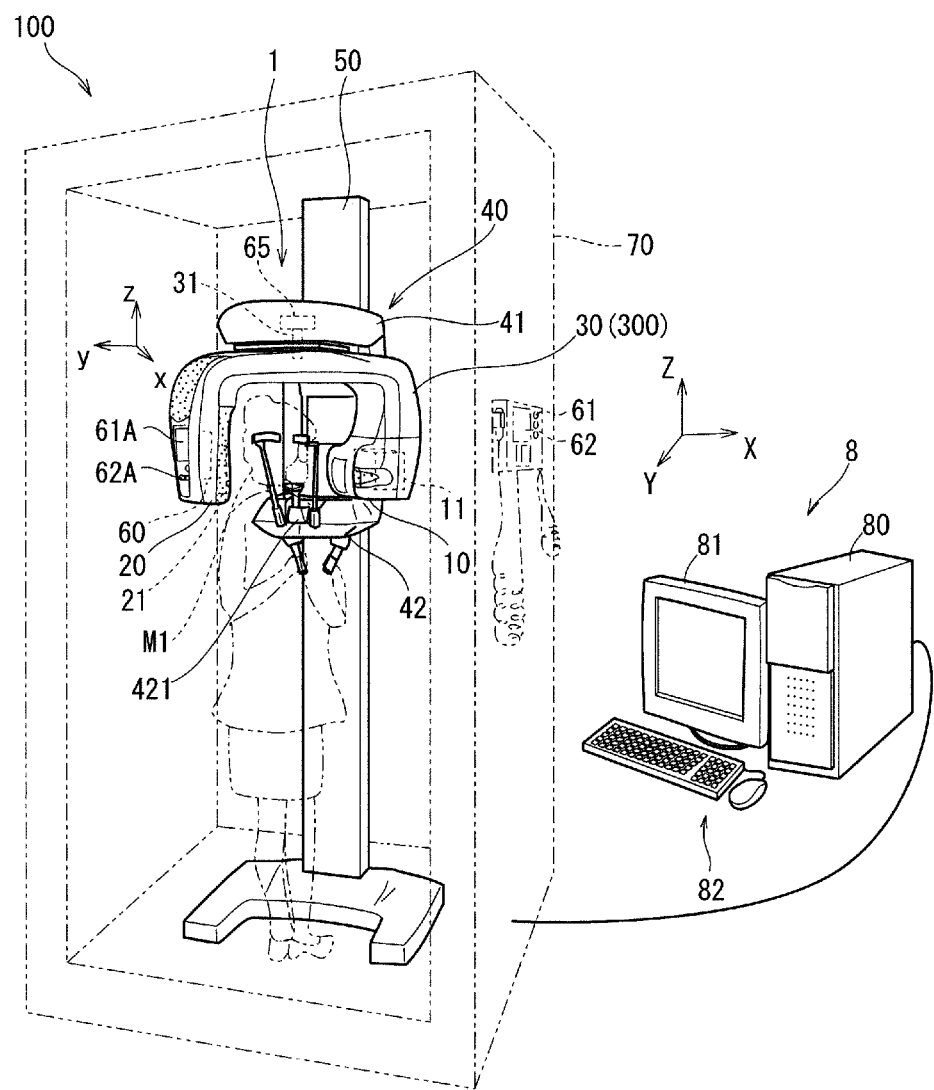
FIG. 1 is a schematic perspective view illustrating an X-ray photography apparatus according to a first preferred embodiment.

Preferred embodiments according to the present invention will now be described with reference to the accompanying drawings. Components described in the preferred embodiments are merely illustrative, and there is no intention to limit the scope of the present invention thereto. In the drawings, the dimensions of components and the number of components are shown in exaggeration or in simplified form, as appropriate, for the sake of easier understanding.

First Preferred Embodiment

FIG. 1 is a schematic perspective view illustrating an X-ray photography apparatus 100 according to a first preferred embodiment. The X-ray photography apparatus 100 is roughly divided into a main body 1 that performs X-ray photography (for example, CT scan) to collect projection image data and an information processing device 8 that produces various images by processing the projection image data collected by the main body 1. The X-ray photography apparatus 100 is configured to be able to perform panorama X-ray photography and head X-ray standard photography (cephalometric photography) in addition to the CT scan.

A left-handed type XYZ-rectangular coordinate system and a left-handed type xyz-rectangular coordinate system are added in FIG. 1. At this point, it is assumed that a "Z-axis direction" is a direction (in this case, a vertical direction) parallel to an axial direction of a turning shaft (rotation axis) 31 of a support 300, it is assumed that an "X-axis direction" is a direction intersecting the Z-axis, and it is assumed that a "Y-axis direction" is a direction intersecting the X-axis and Z-axis directions. The X-axis and Y-axis directions can arbitrarily be defined. At this point, horizontal direction of an object M1 of a subject is defined as the X-axis direction when the subject is positioned in the X-ray photography apparatus 100 to directly confront a post 50, and a front-back direction is defined as the Y-axis direction. Hereinafter, the Z-axis direction is also referred to as a perpendicular direction, and a direction on a two-dimensional plane defined by the X-axis and Y-axis directions is also referred to as a horizontal direction.

The xyz-rectangular coordinate system is a three-dimensional coordinate system defined on a turning support arm 30. At this point, it is assumed that a "y-axis direction" is a direction in which an X-ray generating unit 10 and an X-ray detecting unit 20 face each other, it is assumed that an "x-axis direction" is the horizontal direction orthogonal to the y-axis direction, and it is assumed that a "z-axis direction" is a vertical direction orthogonal to the x-axis and y-axis directions. In the first preferred embodiment, the Z-axis direction and the z-axis direction are directions identical to each other. The support arm 30 of the first preferred embodiment rotates about the turning shaft 31 extending in the vertical direction. Accordingly, the xyz-rectangular coordinate system rotates about the Z-axis (=z-axis) with respect to the XYZ-rectangular coordinate system.

In the first preferred embodiment, as illustrated in FIG. 1, it is assumed that a (+X)-direction is a right-handed direction when the subject directly confronts the post 50, it is assumed that a (+Y)-direction is a rear surface direction, and it is assumed that a (+Z)-direction is an upward direction in the vertical direction. It is assumed that a (+y)-direction is a direction from the X-ray generating unit 10 toward the X-ray detecting unit 20 when the X-ray generating unit 10 and the X-ray detecting unit 20 are viewed from above, it is assumed that a (+x)-direction is a left-handed direction when the subject is oriented toward a (+y) side, and it is assumed that a (+z)-direction is an upward direction in the vertical direction. Accordingly, a (−y)-direction is the direction from the X-ray detecting unit 20 toward the X-ray generating unit 10, a (−x)-direction is the right-handed direction when the subject is oriented toward the (+y) side, and a (−z)-direction is a downward direction in the vertical direction.

Hereinafter, sometimes X, Y, Z, x, y, and z are used to define a two-dimensional coordinate or a plane. For example, it is assumed that an XY-coordinate is the two-dimensional coordinate constructed with an X-coordinate and a Y-coordinate, and it is assumed that an XY-plane is the two-dimensional plane spreading in the X-direction and the Y-direction.

The main body 1 includes the X-ray generating unit 10 that emits an X-ray beam constructed with a bundle of X-rays toward the object M1, the X-ray detecting unit 20 that detects the X-ray, which is emitted from the X-ray generating unit 10 and transmitted through the object M1, the support 300 (support arm 30) that supports the X-ray generating unit 10 and the X-ray detecting unit 20, an elevating unit 40 that can vertically be elevated with respect to the post 50 while suspending the support 300, the post 50 extending in the vertical direction, and a main body controller 60.

The X-ray generating unit 10 and the X-ray detecting unit 20 are suspended from and fixed to both end portions of the support arm 30, and the X-ray generating unit 10 and the X-ray detecting unit 20 are supported so as to face each other. The support arm 30 is suspended from and fixed to the elevating unit 40 with the vertically-extending turning shaft 31.

The X-ray generating unit 10 includes an X-ray generator 11 provided with an X-ray tube of the X-ray source and a housing in which the X-ray generator 11 is accommodated. The housing is attached to the support 300 while being rotatable about the Z-axis. For example, the rotating function is used during the cephalometric photography (see FIG. 2).

The X-ray detecting unit 20 includes a two-dimensional X-ray detector 21 that detects the X-ray transmitted through the object M1. The two-dimensional X-ray detector 21 constitutes an image sensor constructed with plural X-ray detection elements that are disposed so as to spread in a two-dimensional plane (in this case, an xz-plane). The X-ray detection element converts a signal corresponding to an X-ray intensity into an electric signal, and externally outputs the electric signal. The image sensor acquires the intensity of the X-ray incident on the X-ray detecting unit 20 at a required frame rate as frame image data (projection image data expressing an X-ray projection image) in which each pixel has a pixel value corresponding to the X-ray intensity.

In the first preferred embodiment, the support 300 is constructed with the support arm 30 that turns about the turning shaft 31, and the X-ray generating unit 10 and the X-ray detecting unit 20 are attached to the ends of the substantially rectangular parallelepiped support arm 30, respectively. However, the configuration of the support 300 supporting the X-ray generating unit 10 and X-ray detecting unit 20 is not limited to the first preferred embodiment. For example, the X-ray generating unit 10 and the X-ray detecting unit 20 are supported by a cyclic member while facing each other, and the cyclic member may be rotated about an axis passing through the center.

The elevating unit 40 is engaged with the post 50 that is vertically provided so as to extend along the vertical direction. The elevating unit 40 has a substantial U-shape structure, and an upper frame 41 and a lower frame 42 project onto an opposite side to a side on which the elevating unit 40 is engaged with the post 50.

An upper end portion of the support arm 30 is attached to the upper frame 41. Thus, the support arm 30 is suspended from the upper frame 41 of the elevating unit 40, and the support arm 30 moves vertically by the movement of the elevating unit 40 along the post 50.

Object holding means 421 is provided in the lower frame 42. For example, the object holding means 421 is constructed with a rod that fixes the head of the object M1 from both sides, or a chin rest that fixes the jaw. The head of the subject is fixed such that the front-back direction of the head is parallel or substantially parallel to the Y-axis direction.

That is, while the head is fixed, a midsagittal section of the head is parallel or substantially parallel to the YZ-plane defined by the Y-axis and Z-axis directions. The object holding means 421 is not limited to the rod or the chin rest. For example, the object holding means 421 may include a bite block that the object M1 bites to fix the head.

The support arm 30 is elevated by elevating the elevating unit 40, and properly positioned according to a height of the object M1. At this point, the object M1 is fixed to the object holding means 421. In the example of FIG. 1, the object holding means 421 fixes the object M1 such that a body axis of the object M1 becomes identical to or substantially identical to the axial direction of the turning shaft 31.

As illustrated in FIG. 1, the X-ray detecting unit 20 includes the main body controller 60 controlling operation of each configuration of the main body 1. Each configuration of the main body 1 is accommodated in an X-ray protection chamber 70. A display 61, such as a liquid crystal panel, which displays various pieces of information based on the control of the main body controller 60, and an operation panel 62, such as a button, which performs various commands to the main body controller 60, are attached to an outside of a wall of the X-ray protection chamber 70. The operation panel 62 is also used to assign a position of a photographing area of a living body organ. The X-ray photography includes various modes (such as panorama X-ray photography, CT scan, and cephalometric photography), and the mode may be selected by operating the operation panel 62.

In the main body 1, an operation panel 62A having a function identical or similar to the operation panel 62 and a display 61A having a function identical or similar to the display 61 are provided on a rear surface side of the two-dimensional X-ray detector 21 of the X-ray detecting unit 20. Therefore, the main body 1 can be operated on both the inside and the outside of the X-ray protection chamber 70.

For example, the information processing device 8 includes an information processing body unit 80 constructed with a computer or a work station. The information processing device 8 can transmit and receive various pieces of data to and from the main body 1 through a communication cable. Alternatively, the main body 1 and the information processing device 8 may wirelessly conduct data communication with each other.

A display 81 constructed with a display device such as a liquid crystal monitor and an operation unit 82 constructed with a keyboard and a mouse are connected to the information processing body unit 80. An operator can issue various commands to the information processing body unit 80 by performing pointer operation using a mouse on characters or images displayed on the display 81. The display 81 can also be constructed with a touch panel. In this case, the display 81 includes the whole or partial function of the operation unit 82.

Figure 2:
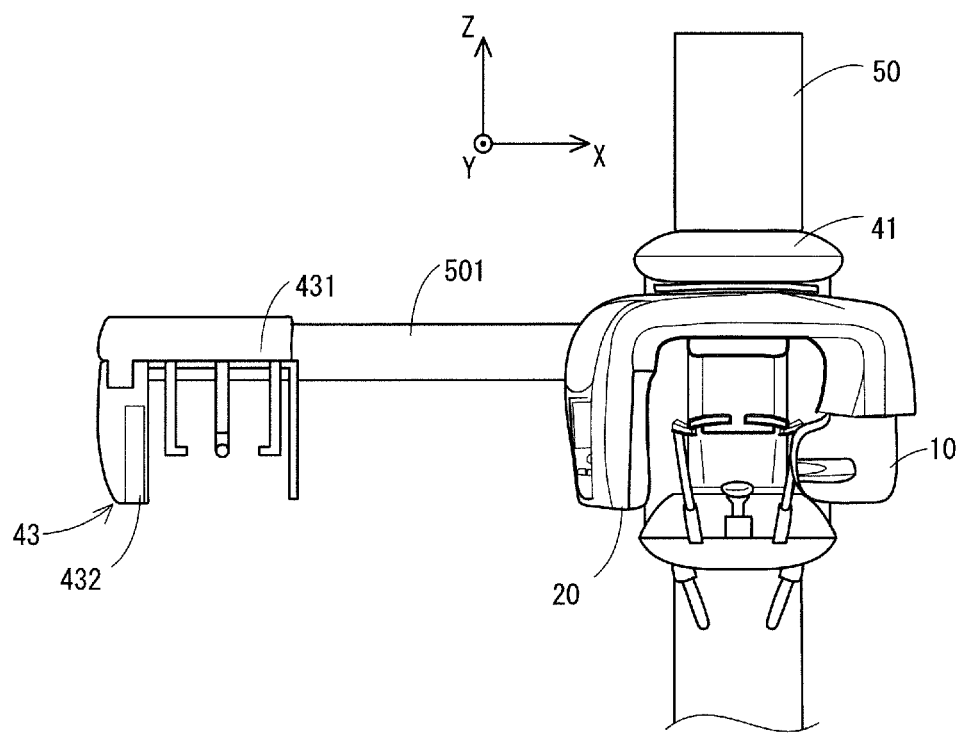
FIG. 2 is a front view illustrating a cephalostat that can be applied to the X-ray photography apparatus.

FIG. 2 is a front view illustrating a cephalostat 43 that can be applied to the X-ray photography apparatus 100. As illustrated in FIG. 2, the cephalostat 43 may be provided in the elevating unit 40. For example, the cephalostat 43 is attached to an arm 501 that extends horizontally from a middle of the post 50. The cephalostat 43 includes a fixture 431 fixing the head to a constant position and a cephalometric X-ray detector 432. Various cephalostats including a cephalostat disclosed in Japanese Patent Application Laid-Open No. 2003-245277 can be used as the cephalostat 43.

Figure 3:
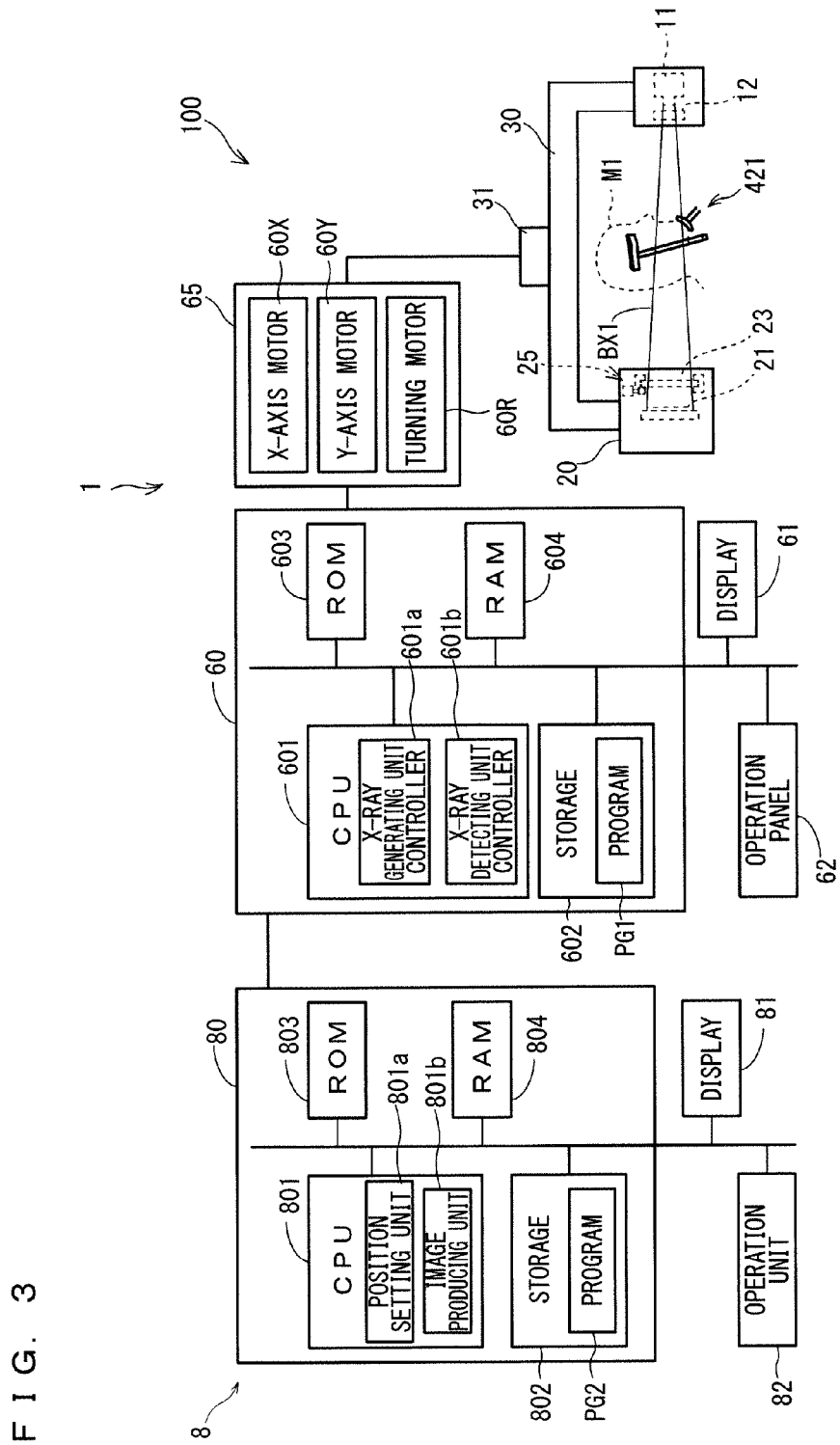
FIG. 3 is a block diagram illustrating a configuration of the X-ray photography apparatus.

FIG. 3 is a block diagram illustrating a configuration of the X-ray photography apparatus 100. As illustrated in FIG.

3, the main body 1 includes a turning mechanism 65 constructed with a turning motor 60R, an X-axis motor 60X, and a Y-axis motor 60Y. The X-axis motor 60X and the Y-axis motor 60Y horizontally move the turning shaft 31 in the X-axis and Y-axis directions through an X-Y moving mechanism (not illustrated), respectively. The X-Y moving mechanism includes an X-direction moving mechanism constructed with a mechanical element displacing the turning shaft 31 in the X-axis direction relative to the object M1 and a Y-direction moving mechanism constructed with a mechanical element displacing the turning shaft 31 in the Y-axis direction relative to the object M1.

The turning motor 60R rotates the turning shaft 31 about the Z-axis through a turning mechanism constructed with a mechanical element rotating the turning shaft 31 relative to the object M1. That is, the turning mechanism 65 horizontally displaces or turnably moves the support arm 30 relative to the object M1 positioned at a required position. In this sense, the turning mechanism 65 is also a moving mechanism that moves the support 300 relative to the object M1. In the first preferred embodiment, the turning mechanism 65 and turning shaft 31 constitute the support moving unit. In the case that it is considered that the displacement of the support 300 in the Z-direction is included in the movement of the support, an elevating motor (not illustrated) that vertically elevates the elevating unit 40 with respect to the post 50 is also included in the turning mechanism 65.

The main body controller 60 is constructed with a CPU 601 and a fixed disk such as a hard disk, and the main body controller 60 has a configuration as a general computer in which a storage 602 storing various pieces of data and a program PG1, a ROM 603, and a RAM 604 are connected to a bus line.

The CPU 601 executes various control programs including the program PG1 controlling the turning mechanism 65. More specifically, the CPU 601 executes the program PG1 stored in the storage 602 on the RAM 604, thereby acting as an X-ray generating unit controller 601a controlling the X-ray generating unit 10 and an X-ray detecting unit controller 601b controlling the X-ray detecting unit 20 according to various photographing modes. The X-ray generating unit controller 601a can control an X-ray irradiation dose, and may have a function of an X-ray irradiation controller. For example, the X-ray detecting unit controller 601b controls an energy conversion unit moving mechanism 25 included in the X-ray detecting unit 20. Since an energy conversion unit corresponds to a filter constitution body in the preferred embodiments according to the present invention as described below, the energy conversion unit moving mechanism 25 is equivalent to a filter constitution body moving mechanism.

The CPU 601 acts as a drive controller that controls drive of the turning mechanism 65. For example, the CPU 601 controls the drive such that the X-ray generating unit 10 and the X-ray detecting unit 20 move on orbits corresponding to various kinds of photographing. The CPU 601 controls the drive of the turning mechanism 65 as the drive controller, thereby controlling the drive of the support moving unit.

The CPU 601 constituting the main body controller 60 and a CPU 801 constituting the information processing body unit 80 integrally constitute the control system of the X-ray photography apparatus 100.

The operation panel 62 connected to the main body controller 60 is constructed with plural operation buttons. In addition to the operation button, a keyboard, a mouse, and a touch pen can be used as an input device instead of or in combination with the operation panel 62. An instruction by voice may be received with a microphone and recognized. The operation panel 62 is an example of operation means (operation unit). Accordingly, the operation means may be configured to receive the operator's operation. The display 61 can also be constructed with a touch panel. In this case, the display 61 includes the whole or partial function of the operation panel 62.

On the display 61, various pieces of information necessary for the operation of the main body 1 are displayed by characters or images. Alternatively, a content displayed on the display 81 of the information processing device 8 may also be displayed on the display 61. Various instructions may be issued to the main body 1 through pointer operation on the characters or images displayed on the display 61 using the mouse.

Figure 4:
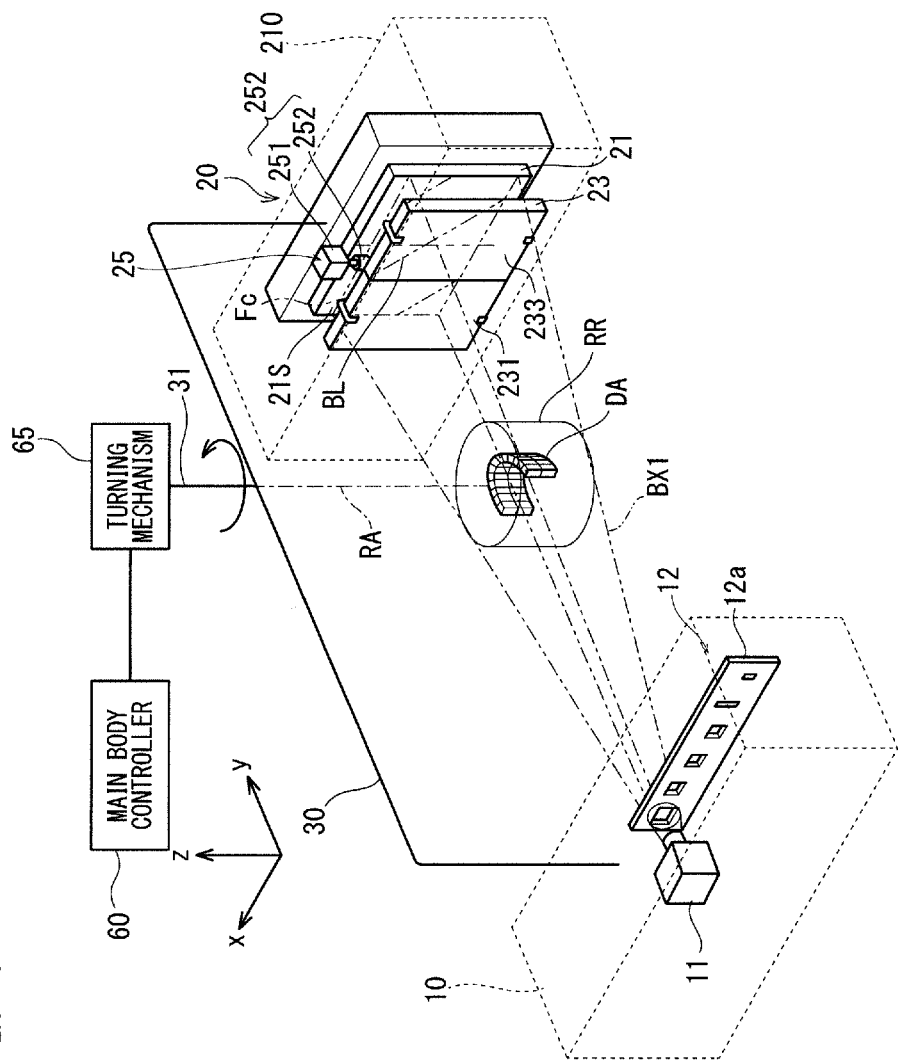
FIG. 4 is a schematic perspective view illustrating CT scan for a jaw performed by a main body.

The main body controller 60 identifies the position of the object M1, and adjusts the orbits of the X-ray generator 11 and two-dimensional X-ray detector 21 during the turning according to the identified position of the object M1. As to a method for identifying the position of the object M1, for example, the head of the object M1 is positioned so that the jaw is fixed by the chin rest with respect to the main body 1 as illustrated in FIG. 4. Therefore, the position of each region (particularly, a jawbone and a tooth) of the head can easily be identified. The same holds true for the case that the bite block is used as the object holding means 421.

In response to an instruction from the operation panel 62 or the information processing device 8, the main body 1 photographs a region of interest (such as a living body organ, a bone (including plural teeth constituting a row of teeth and a jawbone), and a joint) of the object M1 with the X-ray. The main body 1 receives various instruction and the coordinate data from the information processing device 8, and transmits the X-ray projection image data obtained by the photographing to the information processing device 8.

The information processing body unit 80 is constructed with the CPU 801 which performs various kinds of programs and a fixed disk such as a hard disk, and the information processing body unit 80 has a configuration as a general computer in which a storage 802 storing various pieces of data and a program PG2, a ROM 803, and a RAM 804 are connected to a bus line.

The CPU 801 executes the program PG2 stored in the storage 802 on the RAM 804, thereby acting as a position setting unit 801a and an image producing unit 801b. The position setting unit 801a sets the position of the sectional surface according to a shape of the region of interest. More specifically, the position setting unit 801a sets a CT scan area in response to a command based on an operation input through the operation unit 82. The image producing unit 801b produces a CT image by performing image processing of reconstructing the projection image data obtained during the CT scan.

In the first preferred embodiment, as described later, the two pieces of projection image data having the different energy distribution characteristics are obtained with respect to the identical CT scan area. The pieces of projection image data is subjected to the image processing, whereby the CT image corresponding to each energy distribution characteristic is produced in the information processing device 8. Thus, the information processing device 8 is an example of the image processing device.

FIG. 4 is a schematic perspective view illustrating CT scan for a jaw performed by the main body 1. The turning mechanism 65 is connected to the turning shaft 31, and the turning shaft 31 can be rotated by at least 360 degrees. The turning mechanism 65 moves the support arm 30 along the XY-plane. Therefore, the positions of the X-ray generator 11 and the two-dimensional X-ray detector 21 are changed in the XY-plane.

In the first preferred embodiment, the X-ray generator 11 and the two-dimensional X-ray detector 21 are rotated around the object M1 by the turning mechanism 65. Alternatively, the object M1 may be rotated. In this case, a chair on which the object M1 sits is provided, and the chair may be rotated. Therefore, the X-ray generator 11 and the two-dimensional X-ray detector 21 can be turned relative to the object M1.

The X-ray generating unit 10 includes an irradiation field controller 12. The irradiation field controller 12 includes a slit plate 12a disposed in front of the X-ray generator and a moving mechanism sliding the slit plate 12a. Plural slits having different shapes are formed in the slit plate 12a. Based on a control signal from the main body controller 60, the irradiation field controller 12 can select the specific slit from the plural slits by horizontally sliding the slit plate 12a. The X-ray emitted from the X-ray generator 11 is shaped into a substantially pyramid (rectangular section) X-ray cone beam BX1 (rectangular X-ray beam BX1) by passing through the selected rectangular slit. In the case that the panorama X-ray photography or the cephalometric photography is performed, the slit plate 12a moves to a proper position to form a vertically long X-ray slit beam. In the X-ray photography apparatus 100, the panorama X-ray photography or the cephalometric photography is performed with the X-ray slit beam. The irradiation field controller 12 is an example of the X-ray regulating unit.

It is also conceivable that, instead of the slit plate 12a, a slit passing the X-ray is formed by a combination of plural members. In this case, a moving mechanism moving each member is provided, and an aspect ratio of the slit may be controlled by moving each member. Therefore, the spread of the X-ray beam can arbitrarily be adjusted.

Figure 5:
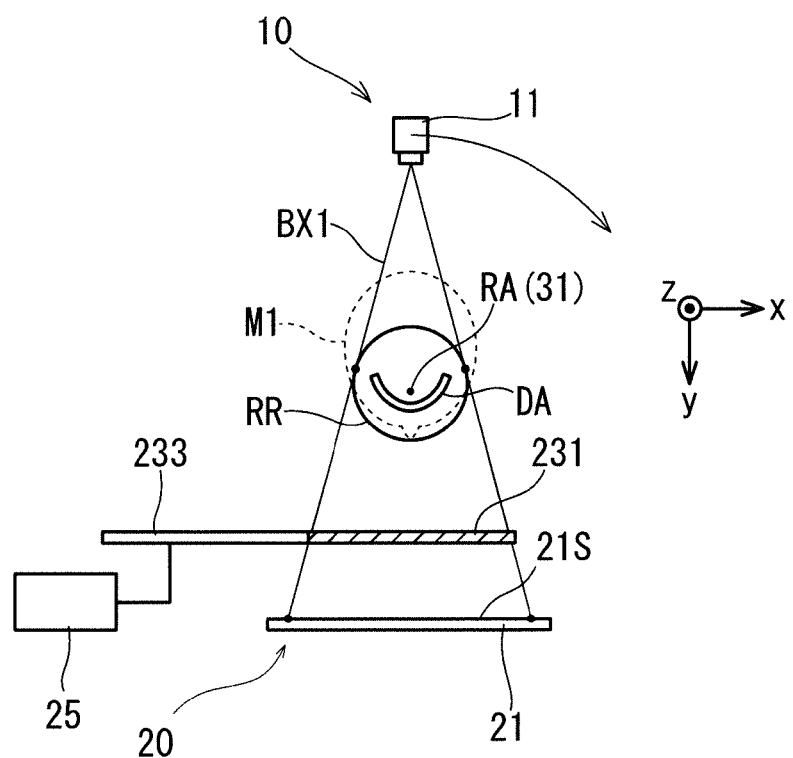
FIG. 5 is a schematic plan view illustrating a main body performing CT scan for a jaw in an object head when the main body is viewed from the object head side along a direction of rotation axes of an X-ray generator and a two-dimensional X-ray detector.

FIG. 5 is a schematic plan view illustrating the main body 1 performing the CT scan for the jaw in the object head when the main body 1 is viewed from a head side of the object M1 along the direction of a rotation axis RA of the X-ray generator 11 and the two-dimensional X-ray detector 21. At this point, the whole jaw of the object M1 is set to a CT scan area RR, and the X-ray cone beam BX1 has a spread including dentitions DA of upper and lower jaws. As used herein, the CT scan area means an area that is always irradiated with the X-ray cone beam BX1 in order to collect the projection image data. The CT scan area RR is formed into a columnar shape in the example of FIG. 5. Therefore, the CT scan area RR has a true circular shape when viewed from above along an axial direction of the turning shaft 31. The planar shape of the CT scan area is not limited to the true circle. For example, the planar shape of the CT scan area may be an ellipse.

In the example of FIG. 5, the rotation axis RA is fixed at the position where the rotation axis RA passes through the inside of a dental arch formed by the dentition DA. The rotation axis RA is aligned with the turning shaft 31 of the support arm 30. While the object M1 is irradiated with the X-ray cone beam BX1, the main body controller 60 drives the turning mechanism 65 to rotate the support arm 30 by a required angle (for example, 360 degrees). Therefore, the projection image projected onto a detection surface 21S of the two-dimensional X-ray detector 21 is collected as projection data of the object M1. The collected projection image data is stored in the storage of the main body controller 60. The projection image data is properly transmitted to the information processing device 8 after or during the CT scan.

During the CT scan, the X-ray generator 11 and the two-dimensional X-ray detector 21 rotate around the object M1 while facing each other with the dentition DA of the region of interest of the object M1 interposed therebetween. At this point, the turning shaft 31 may be fixed to a specific site on the XY-plane, or moved in the XY-plane. In both cases, the rotation axis RA is set to the specific site on the XY-plane during the CT scan. FIG. 5 illustrates the case that the rotation axis constitutes the turning shaft 31.

A configuration of the X-ray detecting unit 20 will be described below. As illustrated in FIGS. 3 and 4, the X-ray detecting unit 20 includes the two-dimensional X-ray detector 21 and an energy conversion unit 23. The X-ray detecting unit 20 is merely indicated by an arrow in FIG. 5. However, FIGS. 3 and 4 will clarify the configuration of the X-ray detecting unit 20. The energy conversion unit 23 is a filter constitution body including at least one filter. In the two-dimensional X-ray detector 21, an X-ray receiving surface receiving the X-ray is formed into a planar shape. In the two-dimensional X-ray detector 21, plural elements outputting generated changes as electric signals are two-dimensionally arrayed on the X-ray receiving surface. For example, the element is made of a cadmium telluride semiconductor or an amorphous selenium semiconductor. The X-ray transmitted through the object M1 is incident on each element made of the semiconductor while converted into the X-rays having the energy distributions different from each other by the filters 231 and 233.

The energy conversion unit 23 is disposed so as to be interposed between the object M1 and the two-dimensional X-ray detector 21. The energy conversion unit 23 is disposed on a path of the X-ray cone beam BX1, or the energy conversion unit 23 is disposed so as to be able to emerge on the path of the X-ray cone beam BX1.

The detection surface 21S of the two-dimensional X-ray detector 21 is not necessarily formed into the planar shape. For example, the detection surface may be formed into a curved surface recessed in the +y direction. Alternatively, one detection surface 21S may be formed by coupling some planar or curved portions.

Instead of including the semiconductor element that directly detects the X-ray, the two-dimensional X-ray detector 21 may be constructed with a scintillator and a semiconductor element that detects light (fluorescence) generated by the incidence of the X-ray on the scintillator.

The energy conversion unit 23 is provided in front of the two-dimensional X-ray detector 21. Two filters 231 and 233 are two-dimensionally arrayed in the energy conversion unit 23, and have different characteristics (conversion characteristics) that convert the energy distribution of the X-ray cone beam BX1. That is, the energy conversion unit 23 is a filter constitution body that includes the filter 231 (first filter) in a first portion while including the filter 233 (second filter) having the conversion characteristic different from that of the filter 231 in a second portion. The first filter 231 has a first energy distribution conversion characteristic, and the second filter 233 has a second energy distribution conversion characteristic. This means that the first portion has the first energy distribution conversion characteristic, and the second portion has the second energy distribution conversion characteristic.

For example, one of the filters 231 and 233 passes the X-ray in a relatively-low-energy region, and the other passes the X-ray in a relatively-high-energy region. For example, different plate materials may be selected from an aluminum plate, a titanium plate, a steel plate, and a copper plate as the filters 231 and 233. The identical plate material may be used as the filters 231 and 233. In this case, the energy distribution of the transmitted X-ray can be varied by changing thicknesses (widths in the y-axis direction) of the filters 231 and 233.

The filters 231 and 233 are provided in front (namely, the −y side) of the two-dimensional X-ray detector 21, and continuously arrayed in the x-axis direction with no gap. More particularly, the filters 231 and 233 are integrally held by a holding mechanism (not illustrated). That is, the energy conversion unit 23 constitutes one plate-like body. In the example of FIG. 4, the filter 231 is disposed on the +X side and the filter 233 is disposed on the −X side.

The X-ray detecting unit 20 includes the energy conversion unit moving mechanism 25 moving the energy conversion unit 23. As illustrated in FIG. 4, the energy conversion unit moving mechanism 25 is constructed with a motor 251, a transmission unit 252, and a guide member. The motor 251 of a driving source moves the energy conversion unit. The transmission unit 252 transmits motion (rotation motion) of the motor to the energy conversion unit 23. The guide member regulates a moving direction of the energy conversion unit 23.

In the CT scan, while the support arm 30 (support 300) rotates, the energy conversion unit moving mechanism 25 moves the energy conversion unit 23 such that the energy conversion unit 23 traverses the X-ray cone beam BX1. In other words, during the X-ray photography, the energy conversion unit moving mechanism 25 moves the energy conversion unit 23 in the direction intersecting a center axis of the X-ray cone beam BX1. In the first preferred embodiment, the energy conversion unit moving mechanism 25 moves the energy conversion unit 23 in the direction (in the example shown in FIG. 4, the x-axis direction parallel to the detection surface 21S) along the detection surface 21S of the two-dimensional X-ray detector 21.

The typical moving direction of the energy conversion unit 23 is parallel to the detection surface 21S. As long as the main body 1 can obtain different pieces of projection image data by causing portions that are different from each other in energy distribution characteristics to pass through an irradiation path of the X-ray beam, the moving direction may be a combination direction in which the direction parallel to the detection surface 21S and a direction orthogonal to the detection surface 21S are combined. Therefore, the moving direction of the energy conversion unit 23 is not always the direction parallel to the detection surface 21S of the two-dimensional X-ray detector 21. That is, the moving direction of the energy conversion unit 23 may be a combination direction in which a two-dimensional direction defined on the two-dimensional detection surface and a direction orthogonal to the detection surface 21S are combined.

The two-dimensional X-ray detector 21, the energy conversion unit 23, and the energy conversion unit moving mechanism 25 are disposed in a chassis 210 of the X-ray detecting unit. The energy conversion unit 23 moves in the chassis 210.

Although not illustrated, the energy conversion unit 23 may include a detaching mechanism that detachably holds the filters 231 and 233. Therefore, the filter is easy to be exchanged. The X-ray photography can be performed with the filter detached.

One of the filters 231 and 233 can be eliminated. In this case, the energy conversion unit is a filter constitution body (first filter constitution body) that includes the filter in the first portion while not including the filter in the second portion. For this filter constitution, the X-rays incident on the portion in which the filter is provided and the portion in which the filter is not provided can differ from each other in the energy distribution conversion characteristic. Therefore, the X-rays incident on the first and second portions can be converted into the X-rays having the energy distribution characteristics different from each other. When the whole X-ray cone beam BX1 passes through the second portion in which the filter is not provided, the X-ray photography can be performed with no use of the filter. By eliminating one of the filters 231 and 233, the first portion has the first energy distribution conversion characteristic, and the second portion has the second energy distribution conversion characteristic.

On the other hand, a second filter constitution body is the filter constitution body that includes the filter 231 (first filter) in the first portion while including the filter 233 (second filter) having the conversion characteristic different from that of the filter 231 in the second portion.

First CT Scan Example

FIGS. 6A to 6E are schematic plan views illustrating a first CT scan example in the X-ray photography apparatus 100 of the first preferred embodiment. In the first CT scan example, the two-dimensional X-ray detector 21 detects the X-ray cone beam BX1 with which the CT scan area RR1 is irradiated through the filters 231 and 233. Hereinafter, sometimes the projection image data obtained through the filter 231 is referred to as first projection image data, and projection image data obtained through the filter 233 is referred to as second projection image data. It is assumed that a is a spread angle (fan angle) in the xy-plane of the X-ray cone beam BX1.

In the first CT scan example, the X-ray generator 11, the two-dimensional X-ray detector 21, and the energy conversion unit 23 are rotated about a center C1 of the CT scan area RR1 (in this case, clockwise). In the following description, the rotation angle is defined while a clockwise direction is set to a positive direction.

Figure 6A:
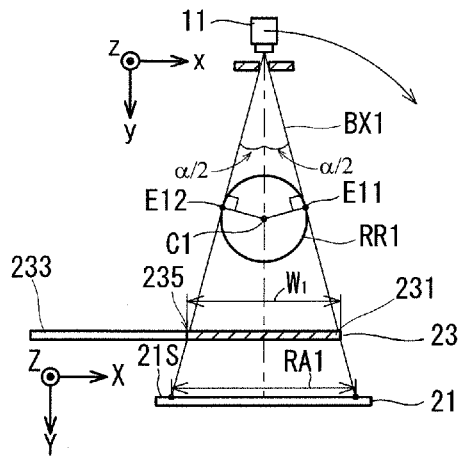
FIGS. 6A to 6E are schematic plan views illustrating a first CT scan example in the X-ray photography apparatus of the first preferred embodiment.
Figure 6B:
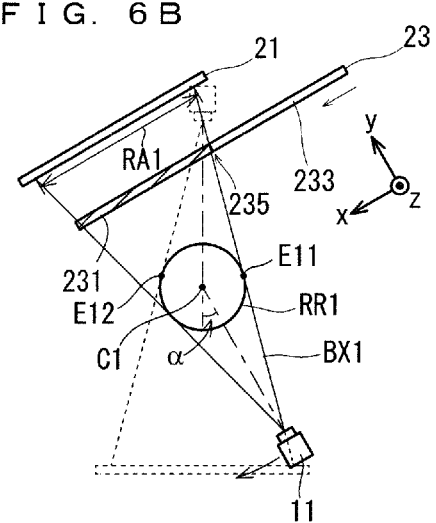
Figure 6C:
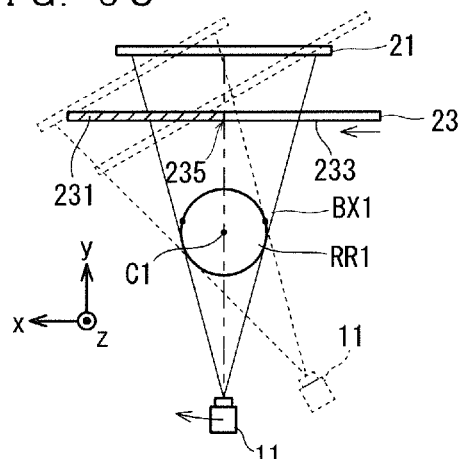
Figure 6D:
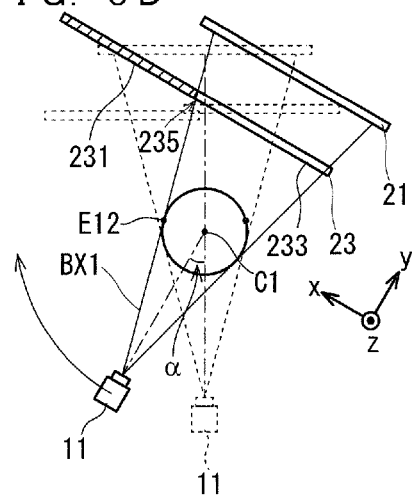
Figure 6E:
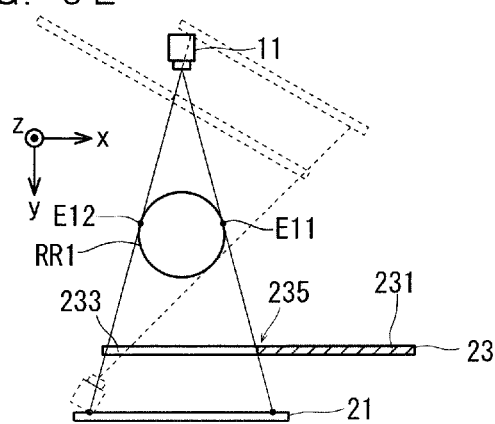

FIG. 6A illustrates a state of the rotation angle of 0 degree, FIG. 6B illustrates a state of the rotation angle of 180−α degrees, FIG. 6C illustrates a state of the rotation angle of 180 degrees, FIG. 6D illustrates a state of the rotation angle of 180+α degrees, and FIG. 6E illustrates a state of the rotation angle of 360 degrees.

Points E11 and E12 in FIG. 6A are points on a contour defining the CT scan area RR1, and a tangent that is in contact with an outer edge of the X-ray cone beam BX1 in the state of the rotation angle of 0 degree. The point E11 is located on the +x side in the CT scan area RR1, and the point E12 is located on the −x side in the CT scan area RR1.

As illustrated in FIG. 6A, immediately after a beginning of the first CT scan example, the energy conversion unit 23 is disposed such that the whole X-ray cone beam BX1 passing through the CT scan area RR1 is incident on the filter 231. At this point, it is assumed that $W_1$ is a width (a length in the x-axis direction) of the filter 231 on which the X-ray cone beam BX1 is incident.

At the beginning of the CT scan, the energy conversion unit 23 is located at the position where a boundary portion 235 between the filters 231 and 233 is irradiated with the X-ray passing through the point E12. The energy conversion unit 23 does not displace the filters 231 and 233 until the rotation angle becomes 180−α degrees in FIG. 6B.

The X-ray generator 11, the two-dimensional X-ray detector 21, and the energy conversion unit 23 rotate integrally from this state, thereby detecting the X-ray through the filter 231 in a predetermined period. Alternatively, the X-ray generator 11 may start the rotation from the position (namely, the side on the −X side compared with the position in FIG. 6A) on the front side in the rotating direction compared with the position in FIG. 6A.

As illustrated in FIG. 6B, when the rotation angle becomes the state of the rotation angle of 180−α degrees from the state of the rotation angle of 0 degree, the outer edge on the −x side of the X-ray cone beam BX1 comes into contact with the point E11 of the CT scan area RR1. The rotation angle changes from 0 degree to 180−α degrees, whereby the point E11 is irradiated with the X-ray from each direction of just 180 degrees. That is, in the CT scan area RR1, first projection image data for 180 degrees is collected with respect to the point E11. The energy conversion unit moving mechanism 25 moves the energy conversion unit 23 in the +x direction when the rotation angle exceeds 180−α degrees. The movement in the +x direction is the movement in the direction corresponding to the moving direction of the two-dimensional X-ray detector 21.

As illustrated in FIG. 6B, when the rotation angle becomes 180−α degrees, the outer edge on the −x side of the X-ray cone beam BX1 is transmitted through the boundary portion 235 between the filters 231 and 233. Because the displacement of the energy conversion unit 23 in the +x direction is simultaneously started, the X-ray passing through the filter 233 is incident on the two-dimensional X-ray detector 21 immediately after the beginning of the movement of the energy conversion unit 23. That is, as illustrated in FIG. 6B, the state of the rotation angle of 180−α degrees is the state in which acquisition of second projection image data is started with respect to the point E11. It is assumed that a whole incident range RA1 is a range where the X-ray cone beam BX1 is incident on the two-dimensional X-ray detector 21. The range where the X-ray cone beam BX1 transmitted through the filter 233 is incident on the two-dimensional X-ray detector 21 spreads gradually from the −x side end toward the +x side in the whole incident range RA1.

A moving amount of the energy conversion unit 23 is proportional to an amount of change in rotation angle. More specifically, the moving amount of the energy conversion unit 23 is set to $W_1/2\alpha$ per rotation angle. Accordingly, the X-ray generator 11, the two-dimensional X-ray detector 21, and the energy conversion unit 23 are rotated by α degrees in the state of the rotation angle of 180 degrees as illustrated in FIG. 6C. The moving amount of the energy conversion unit 23 becomes $W_1/2$. In the X-ray cone beam BX1, a +x side half is incident on the filter 231, and a −x-side half is incident on the filter 233. In the X-ray cone beam BX1, the X-ray passing through the center C1 of the CT scan area RR1 is incident on the boundary portion 235.

As illustrated in FIG. 6D, in the state of the rotation angle of 180+α degrees, the X-ray generator 11, the two-dimensional X-ray detector 21, and the energy conversion unit 23 are rotated by 2α degrees from the state in FIG. 6B. Therefore, the moving amount of the energy conversion unit 23 becomes $W_1$. The filter 233 is displaced by the same moving amount of $W_1$ as the filter 231 in the same direction as the filter 231. Accordingly, the +x side outer edge of the X-ray beam comes into contact with the point E12. In the first CT scan example, at this point, the energy conversion unit moving mechanism 25 completes the movement of the energy conversion unit 23. In this state, the whole X-ray cone beam BX1 passes through the filter 233, and is incident on the two-dimensional X-ray detector 21. In other words, this state is the state in which the acquisition of the second projection image data is started with respect to the point E12. In the first CT scan example, until the rotation angle becomes 360 degrees, the X-ray generator 11 rotates continuously to acquire the projection image data.

FIG. 7 is a view schematically illustrating a sinogram obtained in the first CT scan example of FIGS. 6A to 6E. In FIG. 7, a horizontal axis indicates a position in the x-axis direction of the detection surface 21S of the two-dimensional X-ray detector 21, and a vertical axis indicates the rotation angle. A curved line CL11 indicates a movement locus at a projection position of the point E11, and a curved line CL12 indicates a movement locus at a projection position of the point E12.

As indicated by the curved line CL11, the projection position of the point E11 starts from the +x side end of the whole incident range RA1, and moves gradually toward the −x side. The projection position is located at the −x-side end of the whole incident range RA1 when the rotation angle becomes 180−α degrees. When the X-ray generator 11, the two-dimensional X-ray detector 21, and the energy conversion unit 23 are further rotated, the projection position starts the movement toward the +x side, and the projection position returns to the +x side end of the whole incident range RA1 when the rotation angle becomes 360 degrees.

The projection position of the point E12 can easily be understood from the description of the projection position of the point E11. As indicated by the curved line CL12, the projection position of the point E12 starts from the −x side end of the whole incident range RA1, and moves gradually toward the −x side. The projection position is located at the +x side end of the whole incident range RA1 when the rotation angle becomes 180+α degrees. When the X-ray generator 11, the two-dimensional X-ray detector 21, and the energy conversion unit 23 are further rotated, the projection position starts the movement toward the −x side, and the projection position returns to the −x side end of the whole incident range RA1 when the rotation angle becomes 360 degrees.

As described above with reference to FIGS. 6A to 6E, while the rotation angle changes from 180−α degrees to 180+α degrees, the energy conversion unit 23 moves in the +x direction to start the detection of the X-ray transmitted through the filter 233. Therefore, a first area AR11 (indicated by hatched lines) corresponding to the first projection image data in the whole projection image data and a second area AR12 corresponding to the second projection image data in the whole projection image data exist on the sinogram in FIG. 7. On the sinogram, a straight line L1 connecting the −x side end at the rotation angle of 180−α degrees and the +x side end at the rotation angle of 180+α degrees constitutes a boundary line between the first area AR11 and the second area AR12.

At this point, attention is paid to the projection positions of the points E11 and E12 of the CT scan area RR1. On the sinogram, as indicated by the curved lines CL11 and CL12, the projection positions of the points E11 and E12 move onto the +x side or the −x side after the beginning of the rotation, and move in the opposite direction (the −x side or the +x side) through halfway points (points SP1 and SP2 on the straight line L1), and return to initial positions. Although not illustrated, on the sinogram, the projection position of another specific point (hereinafter, referred to as a "specific point") in the CT scan area RR1 moves in the +x direction or the −x direction according to an increase in rotation angle while a moving width is narrower than the moving widths of the points E11 and E12, returns at a specific rotation angle on the straight line L1, moves in the opposite direction, and returns to the initial projection position.

Thus, the irradiation of a certain specific point with the X-ray just for 180 degrees is completed with respect to the X-ray passing through the filter 231 when the projection position reaches the halfway point (for example, the halfway points SP1 and SP2 for the points E11 and E12) on the straight line L1 since the projection position starts to move. The projection position returns from the halfway point on the straight line L1 to the initial projection position, whereby the irradiation of a certain specific point with the X-ray just for 180 degrees is completed with respect to the X-ray passing through the filter 233. Because the straight line L1 is the boundary line between the first area AR11 and the second area AR12, each of the first area AR11 and the second area AR12 includes the projection image data just for 180 degrees with respect to each specific point.

As described above, in the first CT scan example, what is called a dual energy scan acquiring the first and second pieces of projection image data having the different energy distributions can be performed with respect to the identical CT scan area RR1. With respect to the identical sectional surface, the two kinds of CT images (tomographic images) corresponding to the energy distribution characteristics of the X-rays passing through the filters 231 and 233 can be obtained from the two kinds of pieces of projection image data having the different energy distribution characteristics by the dual energy scan. The information processing device 8 performs the image processing to produce the plural kinds of X-ray images (CT images). For example, difference calculation processing is performed on each CT image to acquire an image of difference, and an image in which a specific region is clearly photographed may be acquired.

When the X-ray cone beam BX1 rotates around the center C1 of the CT scan area RR1 by 360 degrees, each point included in the CT scan area RR1 can be irradiated with the X-ray from each direction of 180 degrees. That is, the two pieces of projection image data having the different energy distributions can be acquired at once with respect to the whole CT scan area RR1 by the CT scan, the dual energy scan can be performed in a relatively short time.

Because the energy conversion unit 23 is moved during the CT scan, the boundary portion 235 between the filters 231 and 233 moves during the CT scan. Therefore, the intensive incidence of the X-ray, which is incident on and scattered by a neighborhood of the boundary portion 235, on a specific position of the two-dimensional X-ray detector 21 can be reduced. For this reason, an influence of the scattered X-ray can be reduced on the CT image. The angles in the description above are defined as 180 degrees (half rotation) and 360 degrees (one rotation) to facilitate understanding of the principle of the CT scan. In reality, CT images can be obtained with slight fluctuations in the angles. Thus, the angles may be defined substantially as 180 degrees and 360 degrees. This holds true for any of the preferred embodiments.

Figure 8A:
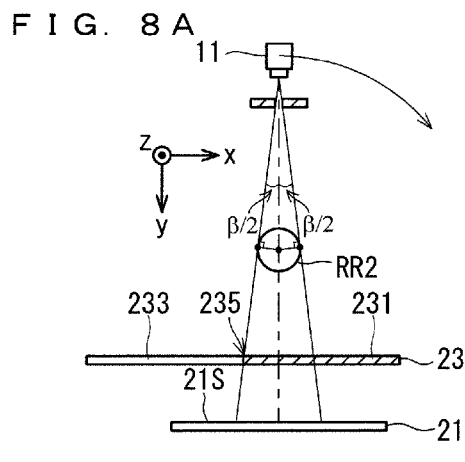
FIG. 8A to 8E are schematic plan views illustrating a modification of the first CT scan example in FIGS. 6A to 6E.
Figure 8B:
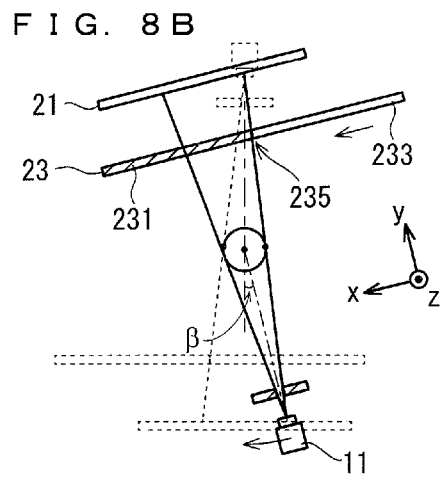
Figure 8C:
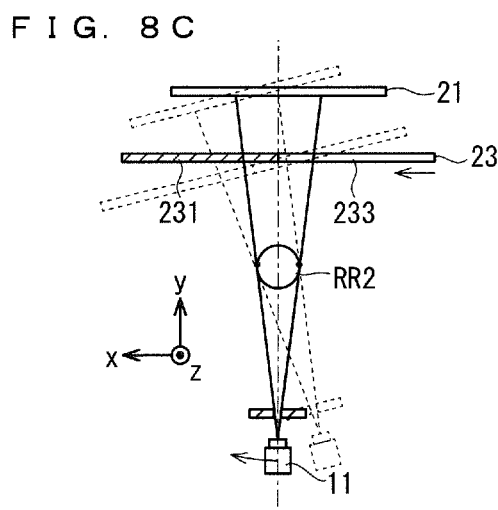
Figure 8D:
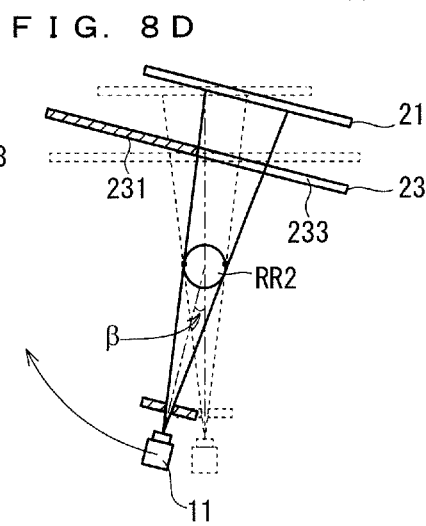
Figure 8E:
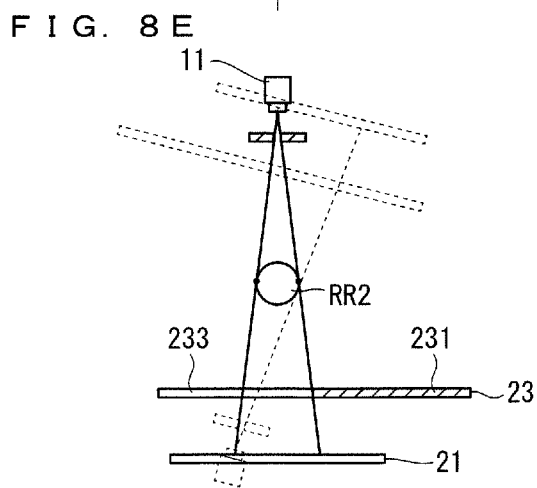

FIGS. 8A to 8E are schematic plan views illustrating a modification of the first CT scan example in FIGS. 6A to 6E. A CT scan area RR2 smaller than the CT scan area RR1 in FIGS. 6A to 6E is photographed by the CT scan in FIG. 8A to 8E. In FIG. 8A to 8E, it is assumed that β is a fan angle of an X-ray cone beam BX2. FIG. 8A illustrates the state in which the X-ray generator 11 has the rotation angle of 0 degree, FIG. 8B illustrates the state of the rotation angle of 180−β degrees, FIG. 8C illustrates the state of the rotation angle of 180 degrees, FIG. 8D illustrates the state of the rotation angle of 180+β degrees, and the FIG. 8E illustrates the state of the rotation angle of 360 degrees.

The fan angle β of the X-ray cone beam BX2 with which the CT scan area RR2 is irradiated is smaller than the fan angle α of the X-ray cone beam BX1 with which the CT scan area RR1 is irradiated.

Even if the CT scan area RR2 is narrow, during the CT scan, the movement control of the energy conversion unit 23 is performed similar to the CT scan area RR1. When the X-ray generator 11 has the rotation angle of 0 degree (the state in FIG. 8A), for example, the energy conversion unit 23 is disposed such that the X-ray cone beam BX1 passes through only the filter 231. The two-dimensional X-ray detector 21 detects only the X-ray cone beam BX1 transmitted through the filter 231 until the rotation angle becomes 180−α degrees (the state in FIG. 8B).

While the rotation angle changes from 180−β degrees to 180+β degrees, the energy conversion unit 23 is moved in the +x direction to gradually switch the filter 231 to the filter 233. The X-ray generator 11 rotates until the rotation angle becomes 360 degrees, and the CT scan is ended.

Even if the CT scan area is small, the dual energy scan can be performed by moving the filters 231 and 233 during the CT scan.

Second CT Scan Example

Figure 9A:
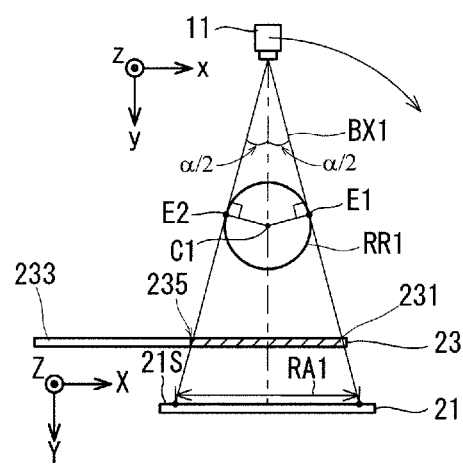
FIGS. 9A to 9F are schematic plan views illustrating a second CT scan example in the X-ray photography apparatus of the first preferred embodiment.
Figure 9B:
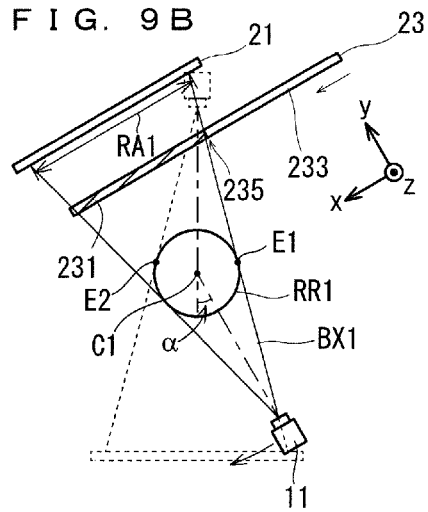
Figure 9C:
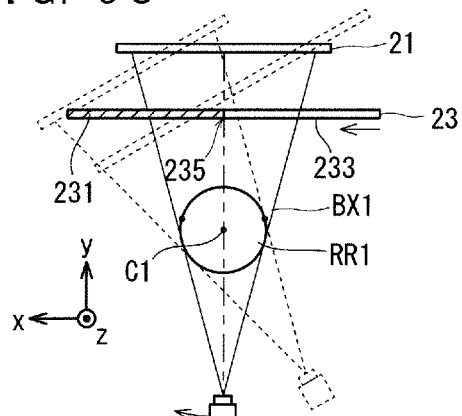
Figure 9D:
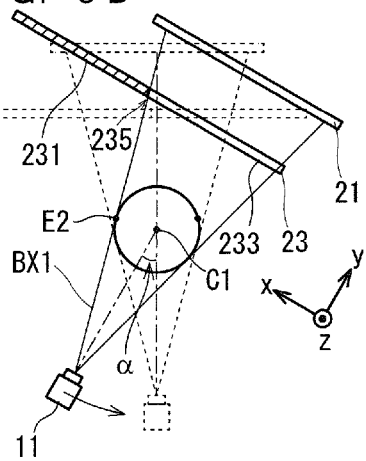
Figure 9E:
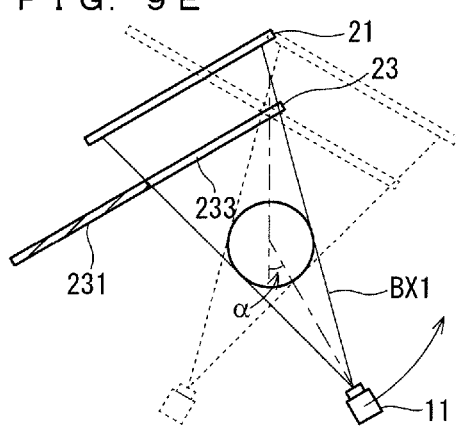
Figure 9F:
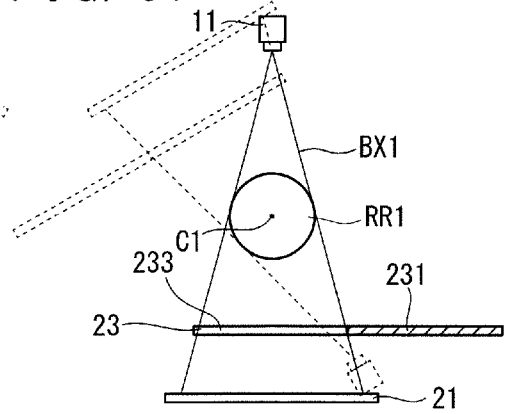

FIGS. 9A to 9F are schematic plan views illustrating a second CT scan example in the X-ray photography apparatus 100 of the first preferred embodiment. FIG. 9A illustrates the state of the rotation angle of 0 degree, FIG. 9B illustrates the state of the rotation angle of 180−α degrees, FIG. 9C illustrates the state of the rotation angle of 180 degrees, FIG. 9D illustrates the state of the rotation angle of 180+α degrees, FIG. 9E illustrates the state of the rotation angle of 180−α degrees, and FIG. 9F illustrates the state of the rotation angle of 0 degree.

In the second CT scan example, as illustrated in FIGS. 9A and 9D, while the rotation angle changes from 0 degree to 180+α degrees, the X-ray generator 11, the two-dimensional X-ray detector 21, and the energy conversion unit 23 rotate similarly to the first CT scan example in FIGS. 6A to 6E, and the energy conversion unit 23 moves relatively in the +x direction. However, as illustrated in FIG. 9D, when the rotation angle becomes 180+α degrees, the rotations of the X-ray generator 11 and two-dimensional X-ray detector 21 are stopped, and the X-ray generator 11 and the two-dimensional X-ray detector 21 are rotated in the opposite direction (in this case, counterclockwise). As illustrated in FIGS. 9E and 9F, the X-ray generator 11 is reversely rotated until the rotation angle becomes 0 degree. The position of the energy conversion unit 23 relative to the X-ray generator 11 and two-dimensional X-ray detector 21 is fixed from the state in FIG. 9D to the state in FIG. 9F.

FIG. 10 is a view schematically illustrating a sinogram obtained in the second CT scan example of FIGS. 9A to 9F. A curved line CL21 indicates the movement locus at the projection position of the point E11, and a curved line CL22 indicates the movement locus at the projection position of the point E12. A first area AR21 indicated by hatched lines is a portion corresponding to the first projection image data in the whole projection image data, and a second area AR22 is a portion corresponding to the second projection image data in the whole projection image data.

In the sinogram of the second CT scan example, the movement locus at the projection position of each point in the CT scan area RR1 is matched with that of the sinogram in FIG. 7 when the rotation angle changes from 0 degree to 180+α degrees. However, in the second CT scan example, the reverse rotation is generated when the rotation angle becomes 180+α degrees. When the rotation angle changes from 180+α degrees to 0 degree, the projection position of each point in the CT scan area RR1 reversely traces the movement locus at the projection position in the change of the rotation angle from 0 degree to 180+α degrees. That is, on the sinogram, the projection positions of the points in the CT scan area RR1 become symmetry in relation to the straight line passing through the rotation angle of 180+α degrees like curved lines CL21 and CL22 that are typically illustrated in FIG. 10.

For the point E12, the projection just for 180 degrees is performed through the filter 231 when the rotation angle changes from 0 degree to 180+α degrees, and the projection just for 180 degrees is performed through the filter 233 when the rotation angle changes from 180+α degrees to 0 degree. That is, the first projection image data and the second projection image data can be acquired in just proportion with respect to the point E12. However, for another point in the CT scan area RR1, the second projection image data is acquired through the filter 233 in excess of 180 degrees. For example, attention is paid to the point E11, the projection image data just for 180 degrees is acquired through the filter 231 when the rotation angle changes from 0 degree to 180−α degrees, and the projection image data just for 180 degrees is acquired through the filter 233 when the rotation angle changes from 180−α degree to 0 degree. While the rotation angle changes from 180−α degrees to 180+α degrees, and while the rotation angle changes from 180+α degrees to 180−α degrees, the identical projection image data is redundantly acquired.

Thus, the pieces of projection image data in which the projection angle partially overlap each other are acquired in the second CT scan example. The overlapping projection image data can be removed in the reconstruction calculation of the CT image. In this case, the reconstruction calculation can be reduced compared with the case that the whole projection image data is used. The overlapping projection image data may be taken in the reconstruction calculation. In this case, the high-reliability CT image can be obtained compared with the CT image reconstructed by the minimum projection image data.

The energy conversion unit moving mechanism 25 may move the energy conversion unit 23 to a withdrawal position from the incident position of the cone beam transmitted through the CT scan area RR1. Therefore, the X-ray photography apparatus 100 can perform both the X-ray photography in which the filters 231 and 233 are used and the X-ray photography in which the filter is not used. In the modification, in the CT scan in which the X-ray generator 11 and the two-dimensional X-ray detector 21 are rotated by one revolution, by properly moving the energy conversion unit 23, the projection image data can be acquired through one of the filters 231 and 233, and the projection image data can be acquired with no use of the filter.

In the first and second CT scan examples, the energy conversion unit 23 is moved in the direction identical to the moving direction (+x direction) of the two-dimensional X-ray detector 21. Alternatively, the energy conversion unit 23 may be moved in the opposite direction (−x direction) to the moving direction of the two-dimensional X-ray detector. In this case, after the X-ray is detected through the filter 233, the energy conversion unit 23 may be moved in the −x direction to detect the X-ray through the filter 231.

Second Preferred Embodiment

A second preferred embodiment will be described below. Hereinafter, the element identical or similar to the already-described element is designated by the identical numeral or a numeral to which a letter is added, and sometimes the detailed description is omitted.

Third CT Scan Example

Figure 11A:
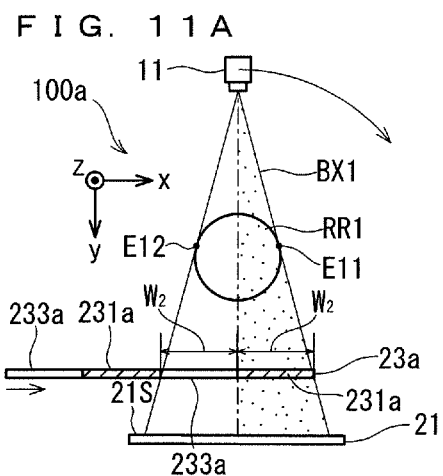
FIGS. 11A to 11E are schematic plan views illustrating a third CT scan example in an X-ray photography apparatus according to a second preferred embodiment.
Figure 11B:
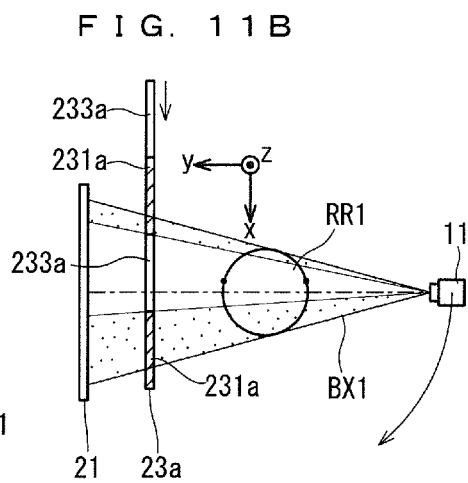
Figure 11C:
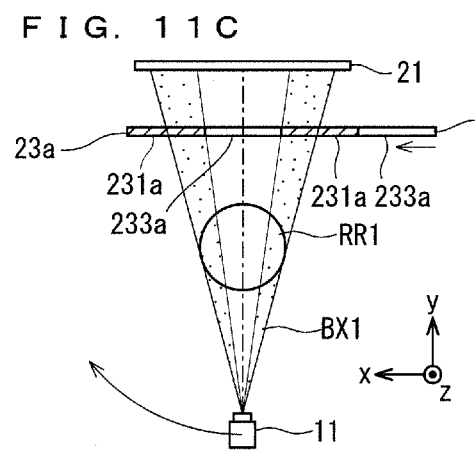
Figure 11D:
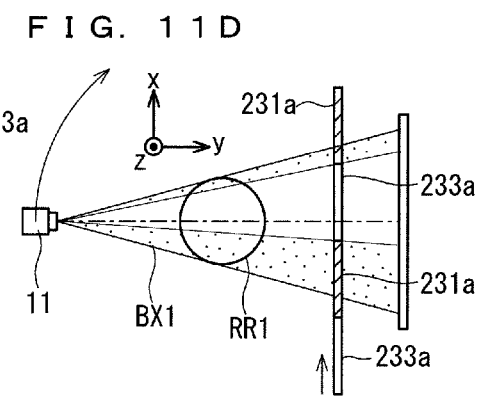
Figure 11E:
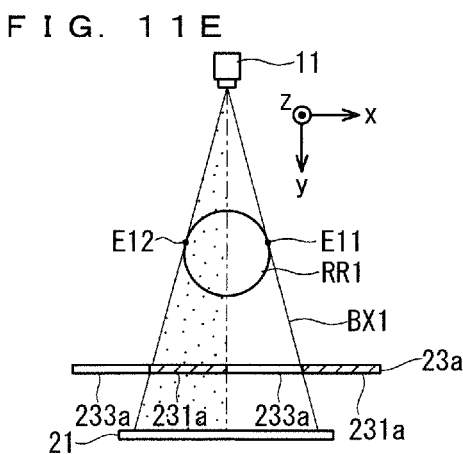
Figure 12A:
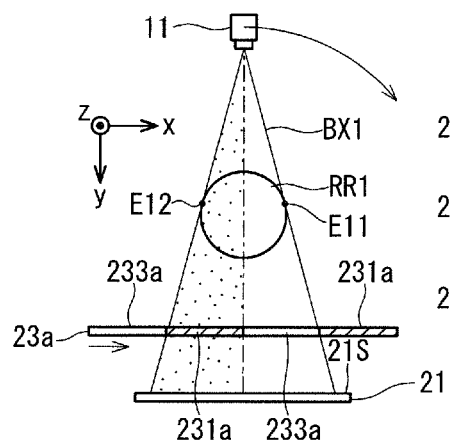
FIGS. 12A to 12E are schematic plan views illustrating the third CT scan example in the X-ray photography apparatus of the second preferred embodiment.
Figure 12B:
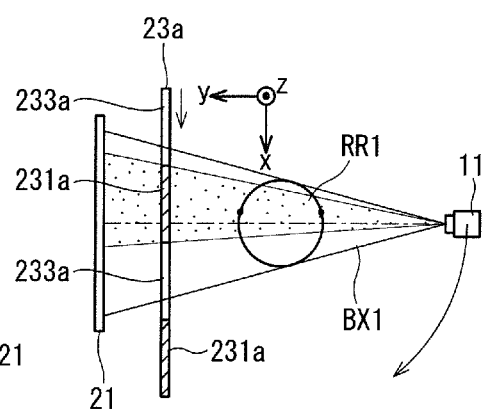
Figure 12C:
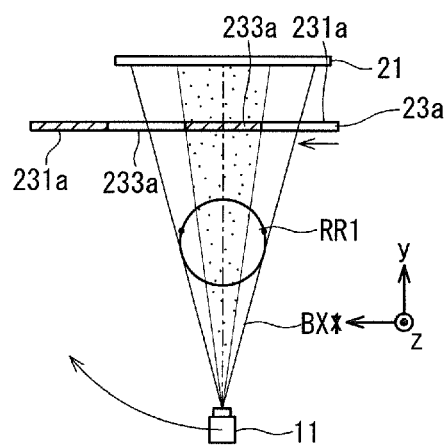
Figure 12D:
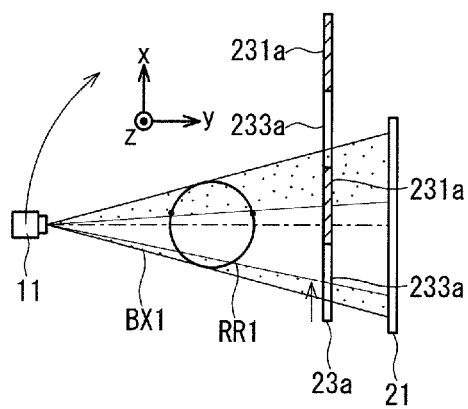
Figure 12E:
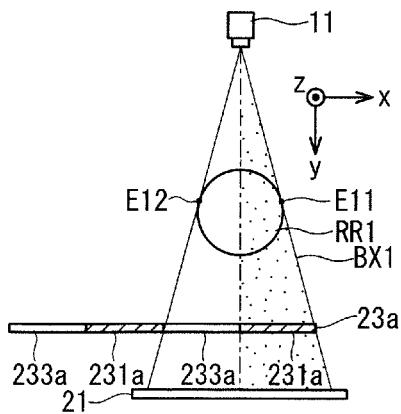

FIGS. 11A to 11E and 12A to 12E are schematic plan views illustrating a third CT scan example in the X-ray photography apparatus 100a according to a second preferred embodiment. FIG. 11A illustrates the state of the rotation angle of 0 degree, FIG. 11B illustrates the state of the rotation angle of 90 degrees, FIG. 11C illustrates the state of the rotation angle of 180 degrees, FIG. 11D illustrates the state of the rotation angle of 270 degrees, and FIG. 11E illustrates the state of the rotation angle of 360 degrees. FIG. 12A illustrates the state of the rotation angle of 360 degrees, FIG. 12B illustrates the state of the rotation angle of 450 degrees, FIG. 12C illustrates the state of the rotation angle of 540 degrees, FIG. 12D illustrates the state of the rotation angle of 630 degrees, and FIG. 12E illustrates the state of the rotation angle of 720 degrees.

In an energy conversion unit 23a of the X-ray photography apparatus 100a of the second preferred embodiment, two filters 231a (first portion) and two filters 233a (second portion) are alternately arrayed into a striped pattern in the x-axis direction. Therefore, the energy conversion unit 23a includes four conversion portions. It is assumed that $W_2$ is a width in the x-axis direction of each of the filters 231a and 233a. Hereinafter, in the two filters 231a and 231a, the filter 231a located on the +x side is referred to as a +x side filter 231a, and the other is referred to as a −x side filter 231a. In the filters 233a and 233a, the filter 233a sandwiched between the +x side filter 231a and the −x side filter 231a is referred to as a +x side filter 233a, and the other is referred to as a −x side filter 233a.

In the third CT scan example, the dual energy scan is performed using the striped energy conversion unit 23a to acquire the CT image. Therefore, as illustrated in FIGS. 11 and 12, the CT scan is rotated by 720 degrees (namely, two revolutions) while the energy conversion unit 23a is moved in the x-axis direction.

More particularly, as illustrated in FIG. 11A, the energy conversion unit 23a is disposed in the state of the rotation angle of 0 degree such that the +x side half of the X-ray cone beam BX1 is incident on the +x side filter 231a while the −x side half is incident on the +x side filter 233a. In the second preferred embodiment, the width in the x-axis direction of the X-ray cone beam BX1 incident on each of the filters 231a and 233a is equal to the width $W_2$ of each of the filters 231a and 233a. The energy conversion unit 23a is moved onto the +x side while the X-ray generator 11 and the two-dimensional X-ray detector 21 are rotated with the center C1 of the CT scan area RR1 as the rotation axis. The moving amount of the energy conversion unit 23a is proportional to the amount of change in rotation angle. More particularly, the moving amount of the energy conversion unit 23a is set to $W_2/360$ per rotation angle.

For example, as illustrated in FIG. 11C, the moving amount becomes $W_2/2$ in the state of the rotation angle of 180 degrees. Therefore, the energy conversion unit 23a is located at the position where the X-ray passing through the center C1 of the CT scan area RR1 passes through the center of the +x side filter 233a. As illustrated in FIG. 11E, the moving amount becomes $W_2$ in the state of the rotation angle of 360 degree, and the +x side portion of the X-ray cone beam BX1 is incident on the +x side filter 233a while the −x side portion is incident on the −x side filter 231a.

Figure 13:
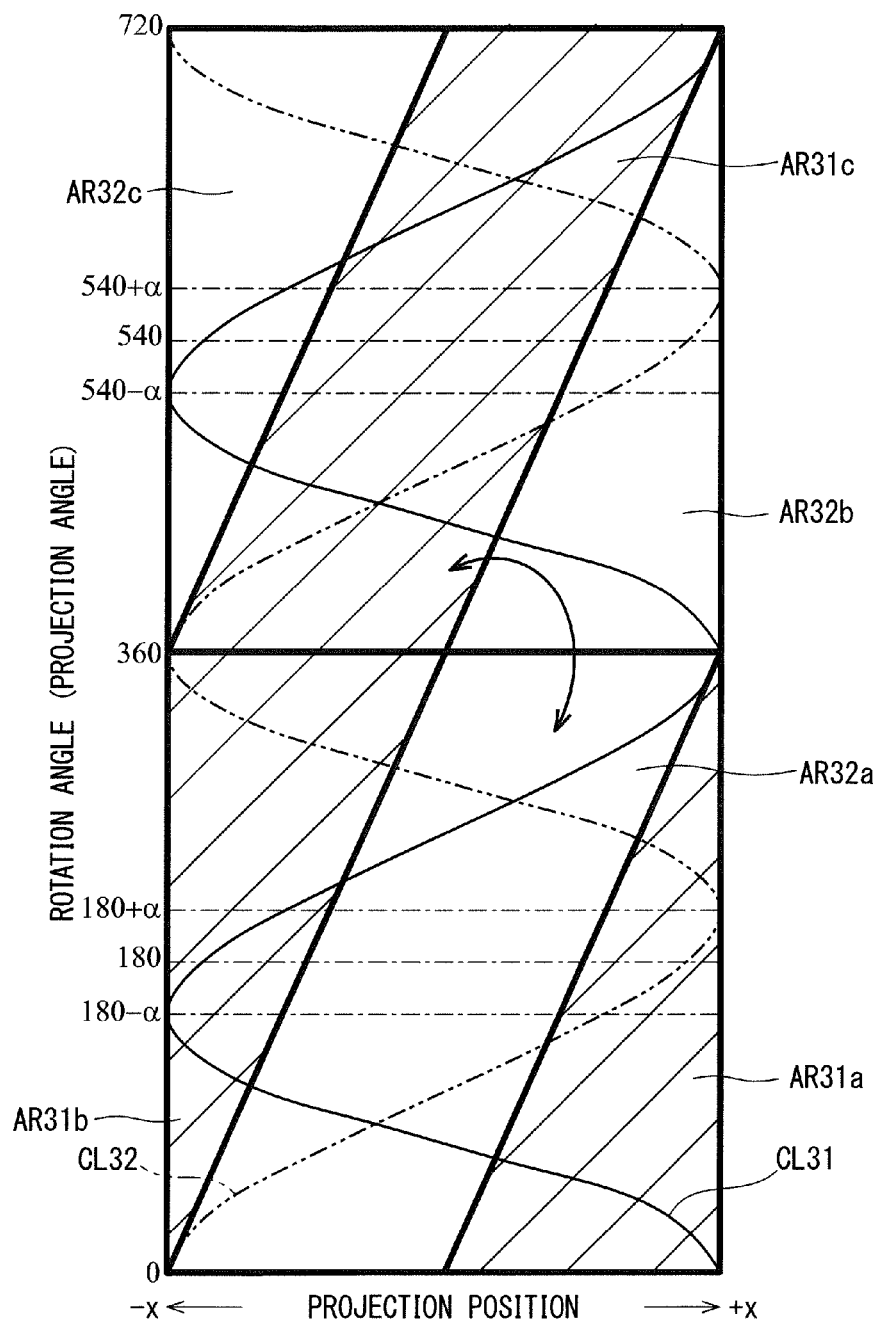
FIG. 13 is a view schematically illustrating a sinogram obtained in the third CT scan example of FIGS. 11 and 12.

FIG. 13 is a view schematically illustrating a sinogram obtained in the third CT scan example of FIGS. 11 and 12. In the sinogram of FIG. 13, a first area portion AR31a indicated by hatched lines corresponds to the first projection image data obtained through the +x side filter 231a in the whole projection image data. First area portions AR31b and AR31c correspond to the first projection image data obtained through the −x side filter 231a in the whole projection image data. Second area portions AR32a and AR32b correspond to the second projection image data obtained through the +x side filter 233a in the whole projection image data. A second area portion AR32c corresponds to the second projection image data obtained through the −x side filter 233a in the whole projection image data.

A curved line CL31 in FIG. 13 indicates the movement locus of the projection position of the point E11. A curved line CL32A indicates the movement locus of the projection position of the point E12. In the curved lines CL31 and CL32, a shape of a curved line portion included in the first area portion AR31c (the rotation angles of 360 degrees to 720 degrees) is identical to a shape of a curved line portion included in the second area portion AR32a (the rotation angles of 0 degree to 360 degrees). That is, the curved line portions of the area portions are considered to be exchangeable.

Figure 14:
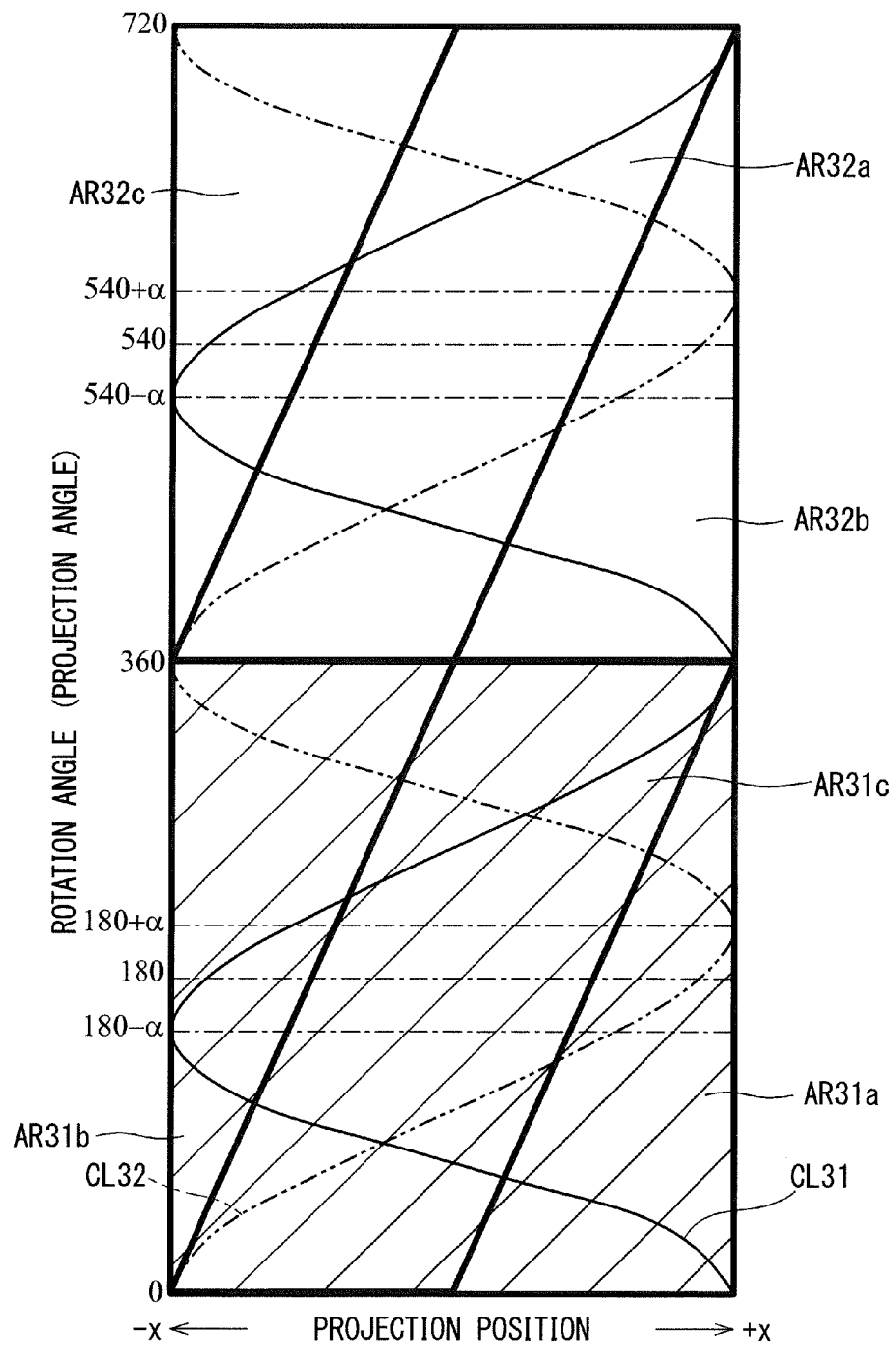
FIG. 14 is a view schematically illustrating a sinogram in which the sinogram in FIG. 13 is rearranged.

FIG. 14 is a view schematically illustrating a sinogram in which the sinogram in FIG. 13 is rearranged. In the sinogram of FIG. 14, the first projection image data for just 360 degrees is acquired with respect to each point of the CT scan area RR1 in the range of 0 degree to 360 degrees, and the second projection image data just for 360 degrees is acquired in the range of 360 degrees to 720 degrees.

When the second preferred embodiment is simply explained, deficit data at rotation angles of 0 degree to 360 degrees is compensated by the next rotation angles of 360 degrees to 720 degrees. Therefore, the moving direction of the energy conversion unit 23 may be set to the direction opposite to that in FIGS. 11 and 12.

In the examples of FIGS. 11 and 12, the +x end of the +x side filter 231a is in contact with the side on the +x side of the X-ray cone beam BX1 at the rotation angle of 0 degree. The energy conversion unit 23 is moved in the +x direction by 2W₂ until the rotation angle of 720 degrees. Therefore, the −x end of the −x side filter 233a is in contact with the side on the −x side of the X-ray cone beam BX1 at the rotation angle of 0 degree. The energy conversion unit 23 may be moved in the −x direction by 2W₂ until the rotation angle of 720 degrees. Even in this case, the energy conversion unit 23 moves along the direction in which the two-dimensional X-ray detector 21 moves.

Thus, the first projection image data for 360 degrees obtained through the two filters 231a and 231a and the second projection image data for 360 degrees obtained through the two filters 233a and 233a are acquired in the CT scan of FIGS. 11 and 12. Accordingly, the dual energy scan can be performed by properly moving the energy conversion unit 23a.

Fourth CT Scan Example

Figure 15:
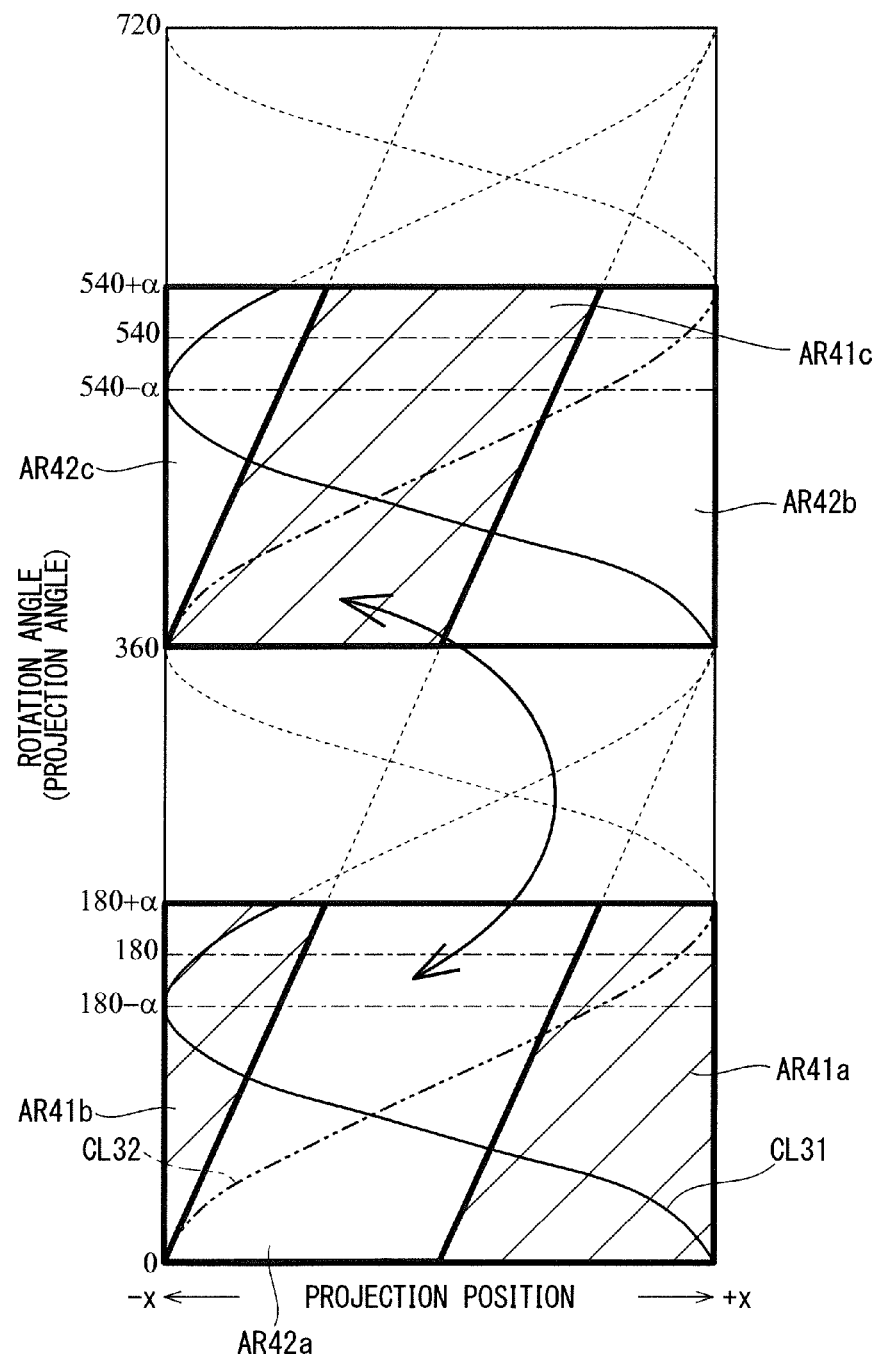
FIG. 15 is a view schematically illustrating a fourth CT scan example in the X-ray photography apparatus of the second preferred embodiment.

FIG. 15 is a view schematically illustrating a fourth CT scan example in the X-ray photography apparatus 100a of the second preferred embodiment. As illustrated in FIG. 15, in the fourth CT scan example, the rotations of the X-ray generator 11 and two-dimensional X-ray detector 21 and the movement in the x-axis direction of the energy conversion unit 23a are performed similarly to the third CT scan example in FIGS. 11 to 14. However, the X-ray is blocked at rotation angles of 180+α degrees to 360 degrees and rotation angles of 540+α degrees to 720 degrees such that the CT scan area RR1 is not irradiated with the X-ray.

On the sinogram in FIG. 15, in the projection image data obtained in the range of 0 degree to 180+α degrees, first area portions AR41a and AR41b indicated by hatched lines correspond to the first projection image data, and a second area portion AR42a corresponds to the second projection image data. In the projection image data obtained in the range of 360 degrees to 540+α degrees, a first area portion AR41c indicated by hatched lines corresponds to the first projection image data, and second area portions AR42b and AR42c correspond to the second projection image data.

The range of 0 degree to 180+α degrees is identical to the range of 360 degrees to 540+α degrees in the movement locus of the projection position of each point included in the CT scan area RR1. The movement locus of the projection position of each point in the first area portion AR41c is matched with the movement locus of the projection position of each point in the second area portion AR42a. Therefore, these areas can be replaced with each other. For this reason, the first area portions AR41a, AR41b, and AR41c correspond to the first projection image data for 180 degrees obtained through the two filters 231a and 231a. The second area portions AR42a, AR42b, and AR42c correspond to the second projection image data for 180 degrees obtained through the two filters 233a and 233a. Thus, the pieces of projection image data for 180 degrees in which the energy distribution characteristics differ from each other can be acquired in the fourth CT scan example.

Fifth CT Scan Example

FIGS. 16A to 16D and 17A to 17D are schematic plan views illustrating a fifth CT scan example in the X-ray photography apparatus 100a of the second preferred embodiment. In the fifth CT scan example, after the X-ray generator 11 and the two-dimensional X-ray detector 21 are rotated by 180+α degrees, the X-ray generator 11 and the two-dimensional X-ray detector 21 are reversely rotated to the original position, and the energy conversion unit 23a is moved onto the +x side. Therefore, in the fifth CT scan example, a ratio of the portion incident on the two filters 231a in the X-ray cone beam BX1 and the portion incident on the filter 233a changes from moment to moment according to the rotation angle.

Figure 16A:
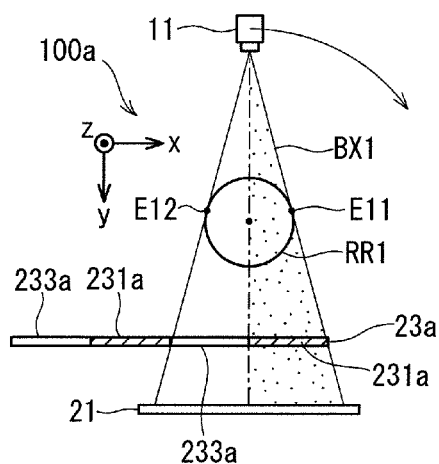
FIGS. 16A to 16D and FIGS. 17A to 17D are schematic plan views illustrating a fifth CT scan example in the X-ray photography apparatus of the second preferred embodiment.
Figure 16B:
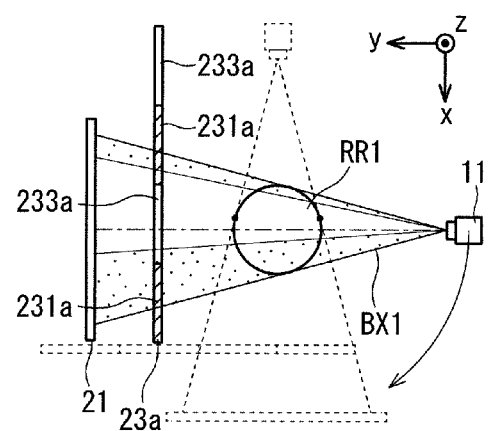
Figure 16C:
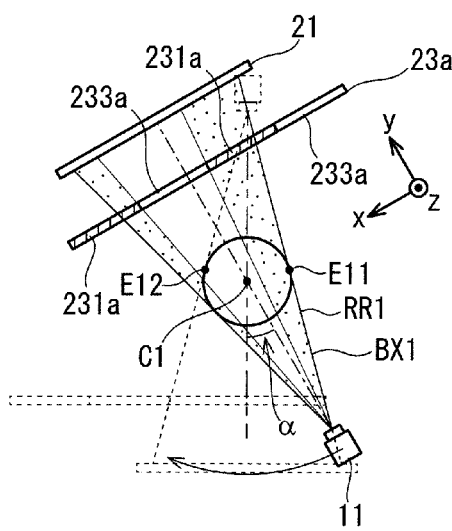
Figure 16D:
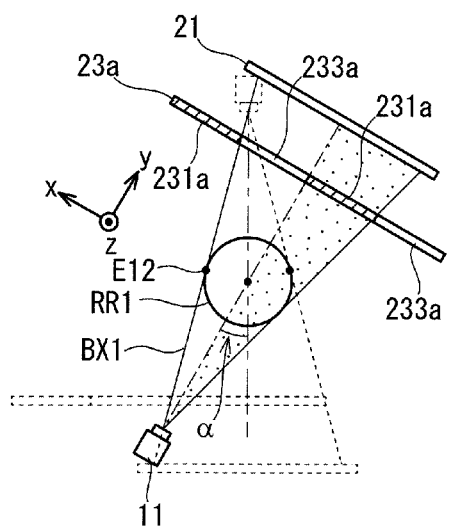
Figure 17A:
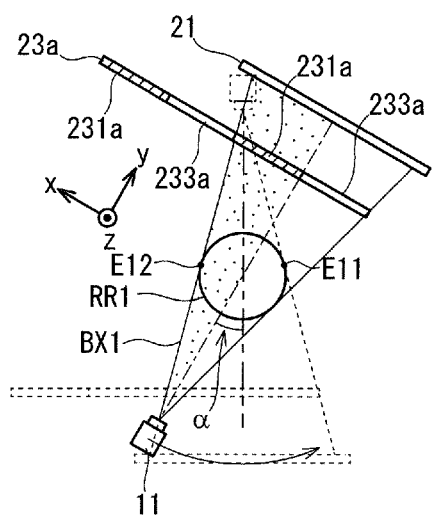
Figure 17B:
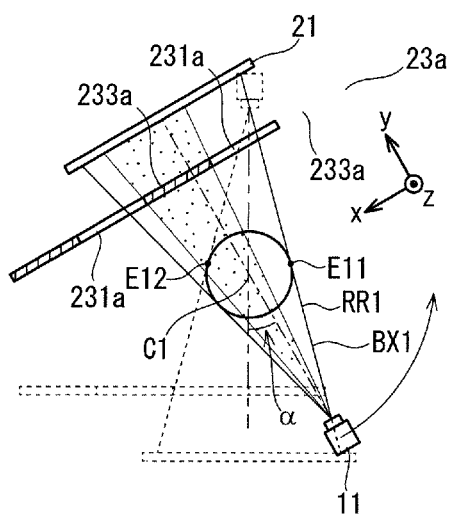
Figure 17C:
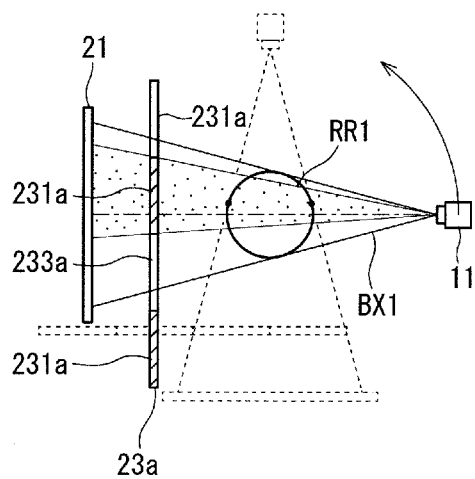
Figure 17D:
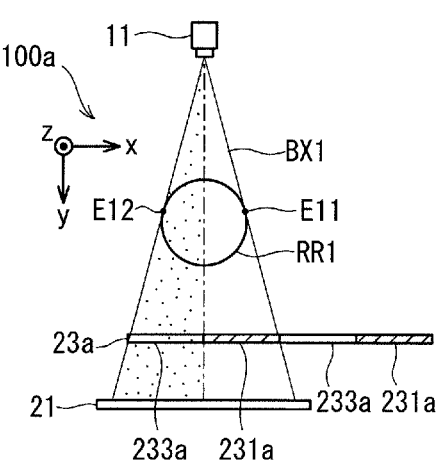

FIGS. 16A to 16D illustrate each state when the X-ray generator 11 is normally rotated from 0 degree to 180+α degrees. FIG. 16A illustrates the state of the rotation angle of 0 degree, FIG. 16B illustrates the state of the rotation angle of 90 degrees, FIG. 16C illustrates the state of the rotation angle of 180−α degrees, and FIG. 16D illustrates the state of the rotation angle of 180+α degrees. FIGS. 17A to 17D illustrate each state when the X-ray generator 11 is reversely rotated from 180+α degrees to 0 degree. FIG. 17A illustrates the state of the rotation angle of 180+α degrees, FIG. 17B illustrates the state of the rotation angle of 180−α degrees, FIG. 17C illustrates the state of the rotation angle of 90 degrees, and FIG. 17D illustrates the state of the rotation angle of 0 degree.

As illustrated in FIGS. 16A to 16D and 17A to 17D, the moving amount of the energy conversion unit 23a is proportional to the amount of change in rotation angle. More specifically, the moving amount is set to $W_2/(180+\alpha)$ per rotation angle. That is, as illustrated in FIG. 16D, at the rotation angle of 180+α degrees, the energy conversion unit 23a moves relatively onto the +x side by the width $W_2$ from the state of the rotation angle of 0 degree, and the X-ray cone beam BX1 is incident on the +x side filter 233a and the −x-side filter 231a. As illustrated in FIG. 17D, when the rotation angle becomes 0 degree by the reverse rotation, the energy conversion unit 23a further moves relatively onto the +x side by the width $W_2$, and the X-ray cone beam BX1 is incident on the −x side filters 231a and 233a.

FIG. 18 is a view schematically illustrating a sinogram obtained in the fifth CT scan example of FIGS. 16 and 17. In the sinogram of FIG. 18, first area portions AR51a, AR51b, and AR51c indicated by hatched lines correspond to the first projection image data, and second area portions AR52a, AR52b, and AR52c correspond to the second projection image data. A curved line CL41 indicates the movement locus at the projection position of the point E11, and a curved line CL42 indicates the movement locus at the projection position of the point E12.

In the fifth CT scan example, the X-ray generator 11, the two-dimensional X-ray detector 21, and the energy conversion unit 23a are reversely rotated after the rotation angle becomes 180+α degrees. Therefore, the movement loci of the projection position of the points in the CT scan area RR1 become symmetric in relation to the line passing through the rotation angle of 180+α degrees on the sinogram in FIG. 18. When the first area portion AR51c and the second area portion AR52a are inverted in relation to the line passing through the rotation angle of 180+α degrees, the first projection image data for 180 degrees is included in the range of 0 degree to 180+α degrees, and the second projection image data for 180 degrees is included in the range of 180+α degrees to 0 degree. Thus, the dual energy scan can be performed in the fifth CT scan example.

Third Preferred Embodiment

Sixth CT Scan Example

Figure 19:
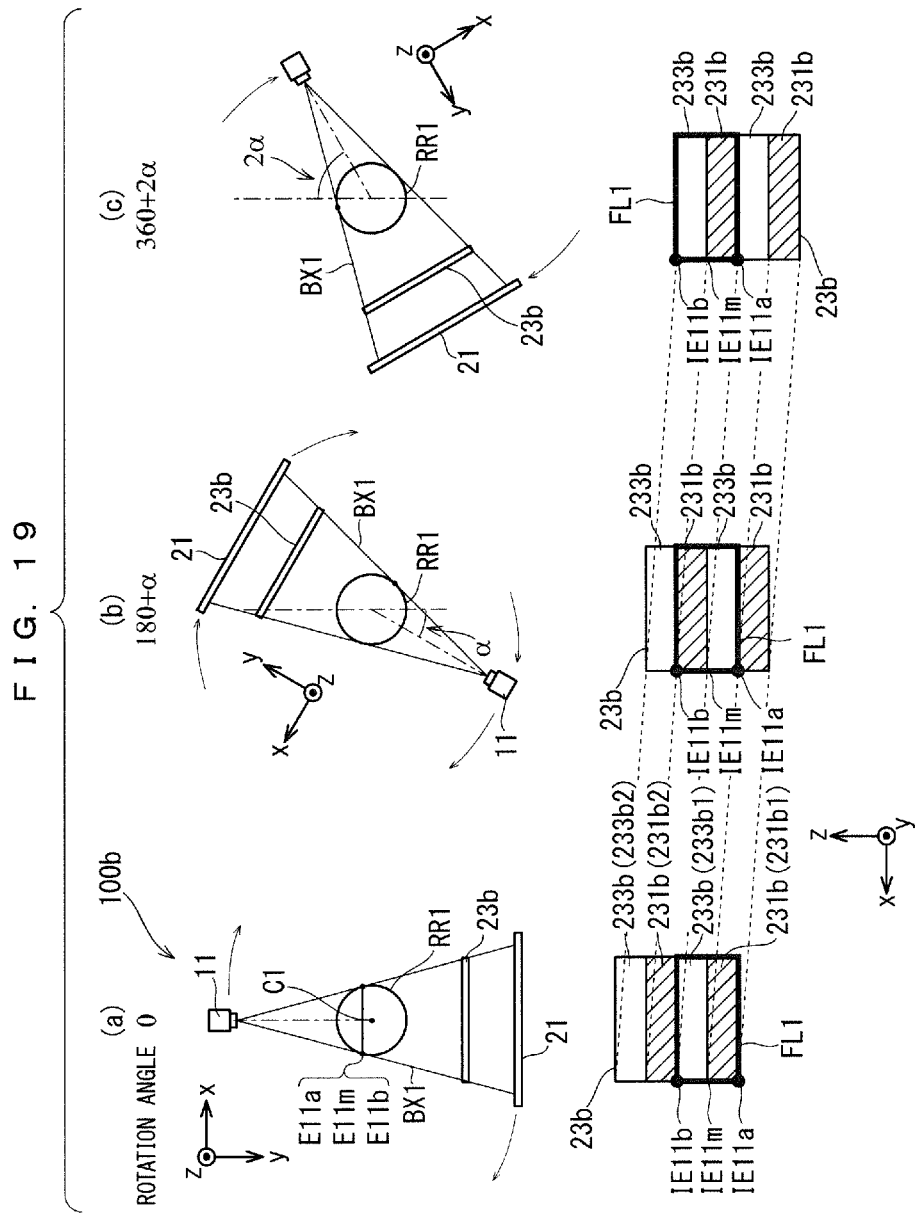
FIG. 19 is a schematic plan view illustrating a sixth CT scan example in an X-ray photography apparatus according to a third preferred embodiment.

FIG. 19 is a schematic plan view illustrating a sixth CT scan example in an X-ray photography apparatus 100b according to a third preferred embodiment. The X-ray photography apparatus 100b of the third preferred embodiment includes an energy conversion unit 23b. The energy conversion unit 23b is a filter constitution body in which two kinds of filters 231b and 233b having different energy conversion characteristics are alternately arrayed in a lengthwise direction (z-axis direction). In other words, the energy conversion unit 23b is configured to sequentially dispose the filters 231b, 233b, 231b, and 233b adjacent to each other from the −z side toward the +z side. In order to distinguish the filters from one another, the filters are referred to as a filter 231b1, a filter 233b1, a filter 231b2, and a filter 233b2 in this order. A lengthwise width of each of the filters 231b and 233b is set to $W_3$.

FIG. 19 illustrates the state of the rotation angle of 0 degree, the state of the rotation angle of 180+α degrees, and the state of the rotation angle of 360+2α degrees.

In the sixth CT scan example, the X-ray generator 11 and the two-dimensional X-ray detector 21 are rotated about the center C1 of the CT scan area RR1 by 360+2α degrees, and the energy conversion unit 23b is moved in the lengthwise direction (Z-axis direction). Specifically, as illustrated at a lower stage in FIG. 19, the energy conversion unit 23b is lowered in the −z direction orthogonal to the moving direction (in this case, the −x direction: although strictly the turning direction of the two-dimensional X-ray detector 21 is arc movement, it is considered that the two-dimensional X-ray detector 21 moves substantially in the −x direction) of the two-dimensional X-ray detector 21 according to the rotation of the X-ray generator 11. A frame border FL1 indicates an area range where the X-ray cone beam BX1 is incident on the energy conversion unit 23b at each rotation angle. The moving amount of the energy conversion unit 23b is proportional to the amount of change in rotation angle. More particularly, in the sixth CT scan example, the moving amount of the energy conversion unit 23b is set to $W_3/(180+α)$ per rotation angle. The frame border FL1 located at the positions of the filters 231b1 and 233b1 at the rotation angle of 0 degree is relatively displaced to the positions of the filters 233b1 and 231b2 at the rotation angle of 180+α degrees (see FIG. 19). A displacement amount of the displacement becomes $W_3$. At the rotation angle of 360+2α degrees, the frame border FL1 is relatively displaced to the positions of the filters 231b2 and 233b2 (see FIG. 19).

At this point, attention is paid to the motion of the filter 233b1. The filter 233b1 is displaced by the displacement amount $W_3$ while the rotation angle changes from 0 degree to 180 degrees, and the filter 233b1 is further displaced by the displacement amount $W_3$ while the rotation angle changes from 180 degrees to 360 degrees. Meanwhile, while the rotation angle changes from 0 degree to 180 degrees, the filter 233b1 or the filter 233b2 moves so as to occupy the remaining portion of the frame border FL1.

The energy conversion unit 23b is disposed in the chassis 210 similarly to the energy conversion unit 23 in FIG. 4. Because of only a difference of the displacement driving configuration in the x-direction or the displacement driving configuration in the z-direction, the disposition of the energy conversion unit 23b in the chassis 210 is not shown.

Attention is paid to points E11a, E11b, and E11m as a representative of each point in the CT scan area RR1. The points E11a and E11b are points on the contour defining the CT scan area RR1, and the tangent that is in contact with the −x side outer edge of the X-ray cone beam BX1 while the rotation angle changes from 0 degree to 360+2α degrees. Accordingly, when viewed in the Z-axis direction, the points E11a and E11b are points moving on the contour circle of the CT scan area RR1 while the rotation angle changes from 0 degree to 360+2α degrees, but not fixed points. It is assumed that the point E11a is a point located at the −z side end (bottom) of the CT scan area RR1, and it is assumed that the point E11b is a point located at the +z side end (top) of the CT scan area RR1. The E11m is a halfway point between the points E11a and E11b.

At the lower stage in FIG. 19, the X-ray passing through the point E11a is incident on the point IE11a located at the −x side end and −z side end on the frame border FL1. The X-ray passing through the point E11b is incident on the point IE11b located at the −x side end and +z side end on the frame border FL1. The X-ray passing through the point E11m is incident on the point IE11m located at the halfway point between the points IE11a and IE11b on the frame border FL1.

As is clear from FIG. 19, the point IE11a is included in the filter 231b1 in the range of 0 degree to 180+α degrees, and the point IE11a is included in the filter 233b1 in the range of 180+α degrees to 360+2α degrees. That is, the X-ray passing through the point E11a is incident on the filter 231b in the range of 0 degree to 180+α degrees, and incident on the filter 233b in the range of 180+α degrees to 360+2α degrees. At the point E11a in the CT scan area RR1, the first projection image data for 180 degrees (for the rotation angle exceeding 180 degrees, namely, at least 180 degrees with respect to another site located at the same level in the z-direction as the point E11a in FIG. 19) is acquired in the range of 0 degree to 180+α degrees, and the second projection image data for 180 degrees (exactly, for the rotation angle exceeding 180 degrees, namely, at least 180 degrees) is acquired in the range of 180+α degrees to 360+2α degrees.

The point IE11m is included in the filter 233b1 in the range of 0 degree to 180+α degrees, and the point IE11m is included in the filter 231b2 in the range of 180+α degrees to 360+2α degrees. That is, the X-ray passing through the point E11m is incident on the filter 233b in the range of 0 degree to 180+α degrees, and incident on the filter 231b in the range of 180+α degrees to 360+2α degrees. At the point E11m in the CT scan area RR1, the second projection image data for 180 degrees (for the rotation angle exceeding 180 degrees, namely, at least 180 degrees with respect to another site located at the same level in the z-direction as the point E11m in FIG. 19) can be acquired in the range of 0 degree to 180+α degrees, and the first projection image data for 180 degrees (exactly, for the rotation angle exceeding 180 degrees, namely, at least 180 degrees) can be acquired in the range of 180+α degrees to 360+2α degrees.

The X-ray that is incident on the point IE11b through the point E11b is incident on the filter 231b and the filter 233b in the same order as the point E11a, the first projection image data for 180 degrees (exactly, rotation angles exceeding 180 degrees) is acquired in the range of 0 degree to 180+α degrees, and the second projection image data for 180 degrees is acquired in the range of 180+α degrees to 360+2α degrees. The detailed description is omitted.

Because the two-dimensional X-ray detector 21 is separated farther from the X-ray generator 11 than the energy conversion unit 23b, the X-ray cone beam BX1 transmitted through the energy conversion unit 23b is enlarged and received on the detection surface of the two-dimensional X-ray detector 21. At this point, it is assumed that a ratio MG1 is a magnification factor of the X-ray cone beam BX1. It is assumed that an area RA1b is a range where the X-ray cone beam BX1 is incident on the detection surface of the two-dimensional X-ray detector 21. That is, the area RA1b is an area where the frame border FL1 is magnified at the ratio MG1.

It is assumed that areas RA1b1, RA1b2, RA1b3, and RA1b4 are areas of the X-rays received on the detection surface of the two-dimensional X-ray detector 21 through the filters 231b1, 233b1, 231b2, and 233b2. The areas RA1b1, RA1b2, RA1b3, and RA1b4 become the areas in which the areas of the filters 231b1, 233b1, 231b2, and 233b2 moving in the frame border FL1 are magnified at the ratio MG1, and similar to the areas of the filters 231b1, 233b1, 231b2, and 233b2 in the frame border FL1, respectively.

Thus, the dual energy scan can be performed in the sixth CT scan example. In the sixth CT scan example, the boundary portions of the filters 231b, 233b, 231b, and 233b move during the CT scan. Therefore, the intensive incidence of the scattered X-ray, which is generated in the boundary portion, on a specific position of the two-dimensional X-ray detector 21 can be reduced. For this reason, an influence of the scattered X-ray can be reduced on the CT image.

Fourth Preferred Embodiment

Figure 20:
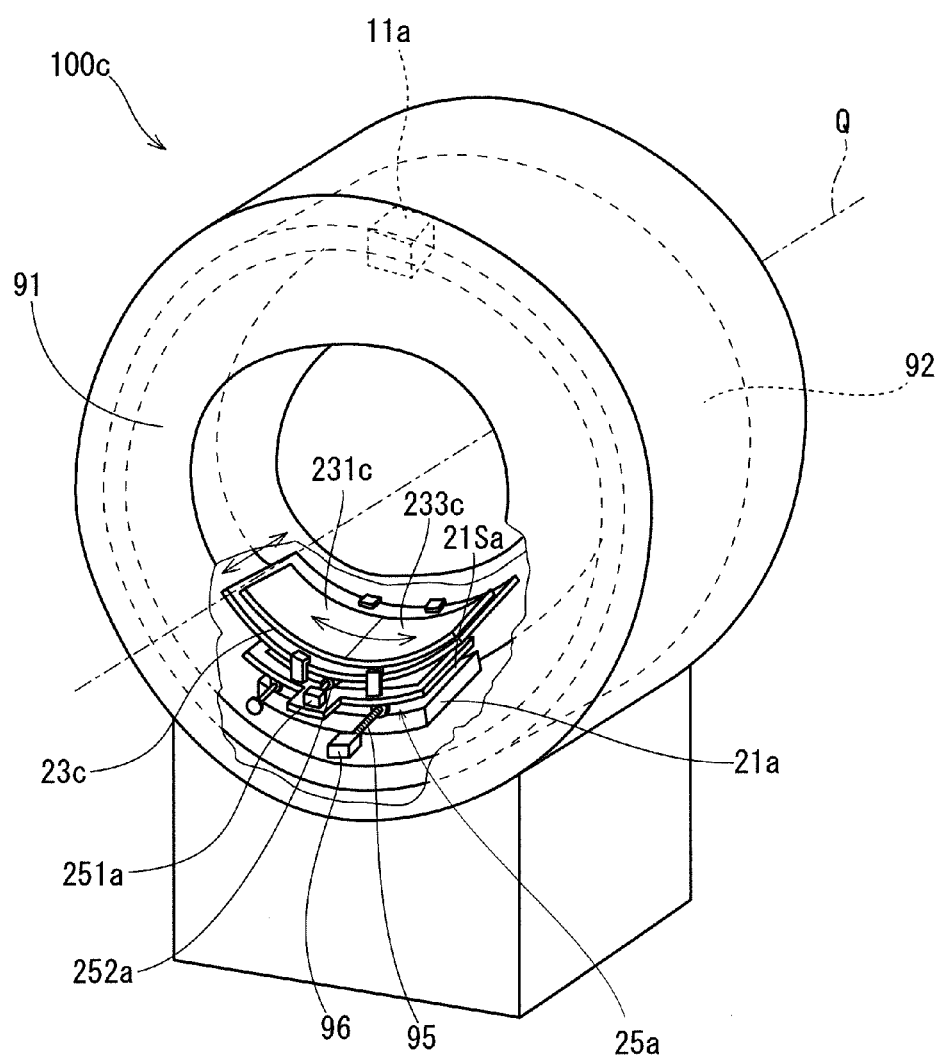
FIG. 20 is a schematic perspective view illustrating an X-ray photography apparatus according to a fourth preferred embodiment.

FIG. 20 is a schematic perspective view illustrating an X-ray photography apparatus 100c according to a fourth preferred embodiment. In FIG. 20, the chassis is partially cut off in order to describe an internal structure of the X-ray photography apparatus 100c. Although not illustrated, in the X-ray photography apparatus 100c, the subject is supported on a stage in a face-up position (or face-down position), and conveyed in a cyclic gantry 91 of the X-ray photography apparatus 100c, and the X-ray photography is performed on the region of interest.

More particularly, a cyclic rotating body 92 is rotatably provided in the gantry 91. An X-ray generator 11a, a two-dimensional X-ray detector 21a, and an energy conversion unit 23c are provided in the rotating body 92. A detection surface 21Sa of the two-dimensional X-ray detector 21a is formed into a curved surface suitable for a curvature of the rotating body 92. The energy conversion unit 23c is a filter constitution body in which filters 231c and 233c having different energy conversion efficiencies are arrayed adjacent to each other along the rotating direction of the rotating body 92. The energy conversion unit 23c is configured to be movable along the rotating direction of the rotating body 92 by an energy conversion unit moving mechanism 25a. For example, the energy conversion unit moving mechanism 25a includes a motor 251a as a driving source moving the energy conversion unit 23c and a transmission unit 252a transmitting the rotation motion of the motor 251a to the energy conversion unit 23c. The transmission unit 252a is constructed with a roller body abutting on the energy conversion unit 23c.

The energy conversion unit moving mechanism 25a may include a rotation-axis-direction moving mechanism that can move the energy conversion unit 23c along a rotation axis Q orthogonal to the rotating direction of the rotating body 92. For example, the rotation-axis-direction moving mechanism is constructed with a ball screw 95 and a motor 96 rotating the ball screw 95. A linear motor may be used as the moving mechanism of the energy conversion unit 23c.

In the X-ray photography apparatus 100c, similarly to the first to fifth CT scan examples described in the first and second preferred embodiments, the rotating body 92 rotates about the rotation axis Q during the X-ray photography, whereby the X-ray generator 11a, the two-dimensional X-ray detector 21a, and the energy conversion unit 23c are rotated to perform the CT scan. The energy conversion unit moving mechanism 25a properly moves the energy conversion unit 23c in the direction traversing the X-ray cone beam emitted from the X-ray generator 11a and the direction along the detection surface 21S of the two-dimensional X-ray detector 21a. Therefore, the first projection image data for 180 degrees through the filter 231c and the second projection image data for 180 degrees through the filter 231c can be acquired with respect to the CT scan area. The energy conversion unit 23c is moved during the CT scan so as to traverse the X-ray cone beam. Therefore, the intensive incidence of the X-ray, which is diffused at the boundary portion between the filters 231c and 233c, on a specific position of the two-dimensional X-ray detector 21a can be reduced. For this reason, an influence of the scattered X-ray can be reduced on the CT image.

In the energy conversion unit 23c of the fourth preferred embodiment, plural filters may be arrayed in the stripe pattern like the energy conversion units 23a and 23b in FIGS. 11 and 19.

5. Modifications

The present invention is not limited to the above preferred embodiments, but various modifications can be made.

Figure 21:
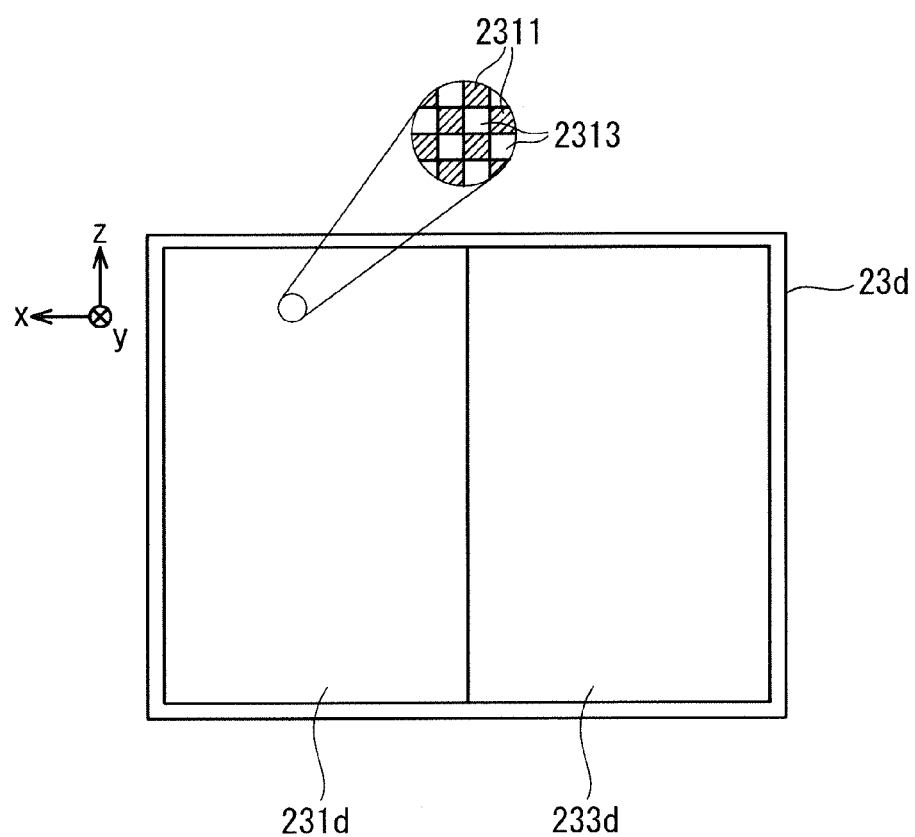
FIG. 21 is a schematic front view illustrating an energy conversion unit according to a modification.

FIG. 21 is a schematic front view illustrating an energy conversion unit 23d according to a modification. The energy conversion unit 23d includes first and second portions that differ from each other in an X-ray energy distribution conversion characteristic. More particularly, a filter 231d is provided in the first portion, and a filter 233d is provided in the second portion.

As illustrated in an enlarged view of FIG. 21, in the filter 231d, two kinds of filter units 2311 and 2313 having the different X-ray energy distribution conversion characteristics are arrayed in a checkered pattern. In other words, in the filter 231d, many filter units 2311 and 2313 are alternately arrayed without a gap in the x-axis and z-axis directions.

In the case that the projection image data is collected using the energy conversion unit 23d, the X-ray transmitted through the filter 231d includes the X-ray in which the energy distribution is converted by the filter unit 2311 and the X-ray in which the energy distribution is converted by the filter unit 2313. The incident position of the two-dimensional X-ray detector can be identified from a positional relationship among the X-ray generator 11, the filter 231d, and the two-dimensional X-ray detector 21 with respect to the X-ray transmitted through the filter unit 2311 and the X-ray transmitted through the filter unit 2313. Therefore, the projection image data based on the X-ray incident on the whole filter unit 2311 and the projection image data based on the X-ray transmitted through the whole filter unit 2313 can be separated and acquired. Accordingly, the two kinds of CT images can be acquired with respect to the identical sectional surface based on the two kinds of pieces of projection image data having the different energy distribution characteristics.

The energy conversion units of the preferred embodiments have the filter configuration including the two portions having the conversion characteristics different from each other. Alternatively, the filter configuration may include at least three portions having the conversion characteristics different from one another. In this case, the energy conversion unit is moved during the CT scan, and the two-dimensional X-ray detector detects the X-ray transmitted through the CT scan area through at least three portions, which allows the performance of the multi energy scan acquiring at least three pieces of projection image data having the energy distribution characteristics different from one another.

The CT scan is performed on the head (particularly, jaw) of the object M1 using the X-ray photography apparatus 100 of the preferred embodiment. Additionally, the present invention is effective in performing the CT scan on other regions (such as an ear, a nose, a throat, various viscera, and arms and legs) of a human body. In the X-ray photography apparatus 100 of the preferred embodiment, during the CT scan, the X-ray generator 11 and the two-dimensional X-ray detector 21 rotate while a constant height is kept relative to the object M1 (particularly, the position in the body axis direction (Z-axis direction) of the object M1 is kept constant). Alternatively, in the X-ray photography apparatus of the present invention, the X-ray generator and the two-dimensional X-ray detector rotate while the position in the body axis direction of the object M1 changes relatively, whereby the X-ray generator and the two-dimensional X-ray detector may relatively rotate in a spiral manner.

While the invention has been shown and described in detail, the foregoing description is in all aspects illustrative and not restrictive. It is therefore understood that numerous modifications and variations can be devised without departing from the subject-matter of the claims.

What is claimed is:

1. An X-ray photography apparatus comprising:
   an X-ray generator that generates and emits an X-ray beam to be transmitted through an object;
   a two-dimensional X-ray detector that receives and detects the X-ray beam;
   a support that supports the X-ray generator and the two-dimensional X-ray detector while the X-ray generator and the two-dimensional X-ray detector are arranged opposite each other;
   a moving mechanism that turns the support relative to the object while the object is interposed between the X-ray generator and the two-dimensional X-ray detector;
   a filter constitution body that is interposed between the object and the two-dimensional X-ray detector in a path of the X-ray beam, a first portion and a second portion being two-dimensionally arrayed in the filter constitution body, the first portion having a first energy distribution conversion characteristic of the X-ray beam, the second portion having a second energy distribution conversion characteristic of the X-ray beam; and
   a filter constitution body moving mechanism that moves the filter constitution body in a direction along a detection surface of the two-dimensional X-ray detector such that the filter constitution body traverses the X-ray beam during turning of the support during X-ray photography.

2. The X-ray photography apparatus according to claim 1, wherein the first portion includes a filter while the second portion does not include a filter.

3. The X-ray photography apparatus according to claim 1, wherein
   the first portion includes a first filter, the first filter having the first energy distribution conversion characteristic, and
   the second portion includes a second filter, the second filter having the second energy distribution conversion characteristic.

4. The X-ray photography apparatus according to claim 1, wherein the filter constitution body moving mechanism includes a motor and a transmission unit.

5. The X-ray photography apparatus according to claim 1, wherein the filter constitution body moving mechanism moves the filter constitution body between the two-dimensional X-ray detector and the object and in a vertical direction along a rotational axis of the support or in a horizontal direction orthogonal to the rotational axis of the support.

6. The X-ray photography apparatus according to claim 5, wherein
   the X-ray photography is CT scan, and
   the first portion and the second portion are arrayed in a striped pattern.

7. The X-ray photography apparatus according to claim 5, wherein
   the X-ray photography is CT scan, and
   the first portion and the second portion are arrayed in a checkered pattern.

8. The X-ray photography apparatus according to claim 6, wherein the filter constitution body moving mechanism and the two-dimensional X-ray detector are disposed in a chassis.

9. The X-ray photography apparatus according to claim 8, wherein the filter constitution body moves in a direction intersecting a moving direction of the two-dimensional X-ray detector in the chassis.

10. The X-ray photography apparatus according to claim 8, wherein the filter constitution body moves in a direction along or facing a moving direction of the two-dimensional X-ray detector in the chassis.

11. The X-ray photography apparatus according to claim 1, further comprising an irradiation field controller that regulates the X-ray beam emitted from the X-ray generator,
wherein the irradiation field controller shapes the X-ray beam into an X-ray cone beam.

12. The X-ray photography apparatus according to claim 11, wherein
the X-ray photography is CT scan, and
the filter constitution body moving mechanism withdraws the filter constitution body from a position on which the X-ray cone beam transmitted through a CT scan area is incident.

13. The X-ray photography apparatus according to claim 11, wherein panorama X-ray photography or cephalometric photography is performed using an X-ray slit beam formed by the irradiation field controller.

14. The X-ray photography apparatus according to claim 9, wherein, when the filter constitution body moving mechanism moves the filter constitution body during CT scan,
at least one of the first portion and the second portion is displaced by a width in the intersecting direction while the support turns substantially 180 degrees plus a fan angle of the X-ray beam,
while the support further turns substantially 180 degrees plus a fan angle of the X-ray beam, the one is further displaced by the width in the intersecting direction, and the other of the first portion and the second portion receives a remaining X-ray beam, the remaining X-ray beam not including an X-ray beam incident on the one displaced.

15. The X-ray photography apparatus according to claim 10, wherein, when the filter constitution body moving mechanism moves the filter constitution body during the CT scan,
during rotation of the support, the first portion is displaced by a width of the first portion in the moving direction of the two-dimensional X-ray detector, and the second portion is displaced by the same width in the displacement direction of the first portion at the same time as the first portion is displaced.

16. An image processing device that processes image data acquired by the X-ray photography apparatus according to claim 1, the image processing device comprising an image processor that performs image processing on pieces of image data to produce X-ray images corresponding to each of energy distribution characteristics, the pieces of image data being obtained by detecting the X-ray beams using the two-dimensional X-ray detector, the X-ray beams being transmitted or passing through the first portion and the second portion of the filter constitution body.

17. The image processing device according to claim 16, wherein
the image processor acquires an image of difference of the image data corresponding to each of the energy distribution characteristics, the image of difference being produced by calculation.

18. An X-ray photography method comprising:
rotating, about an object, an X-ray generator and a two-dimensional X-ray detector facing each other, the X-ray generator generating an X-ray beam, the two-dimensional X-ray detector detecting the X-ray beam transmitted through the object; and
moving, during the rotating, a filter constitution body in a direction along a detection surface of the two-dimensional X-ray detector such that the filter constitution body traverses the X-ray beam, the filter constitution body being interposed between the object and the two-dimensional X-ray detector in a path of the X-ray beam, a first portion and a second portion being two-dimensionally arrayed in the filter constitution body, the first portion having a first energy distribution conversion characteristic of the X-ray beam, the second portion having a second energy distribution conversion characteristic of the X-ray beam.

* * * * *